(12) United States Patent
Muir et al.

(10) Patent No.: US 6,875,594 B2
(45) Date of Patent: Apr. 5, 2005

(54) METHODS OF LIGATING EXPRESSED PROTEINS

(75) Inventors: Tom W. Muir, New York, NY (US); Philip A. Cole, New York, NY (US); Dolan Sondhi, New York, NY (US); Konstantine Severinov, New York, NY (US)

(73) Assignee: The Rockefeller University, New York, NY (US)

( * ) Notice: Subject to any disclaimer, the term of this patent is extended or adjusted under 35 U.S.C. 154(b) by 297 days.

(21) Appl. No.: 09/904,117

(22) Filed: Jul. 12, 2001

(65) Prior Publication Data

US 2002/0151006 A1 Oct. 17, 2002

Related U.S. Application Data

(63) Continuation of application No. 09/191,890, filed on Nov. 13, 1998, now abandoned.
(60) Provisional application No. 60/065,391, filed on Nov. 13, 1997, and provisional application No. 60/093,990, filed on Jul. 24, 1998.

(51) Int. Cl.[7] ............................. C12N 9/00; C07K 14/00
(52) U.S. Cl. ..................... 435/183; 435/69.1; 435/69.7; 435/172.3; 530/334; 530/350
(58) Field of Search ............................... 435/69.1, 69.7, 435/172.3, 183; 530/334, 350

(56) References Cited

U.S. PATENT DOCUMENTS 5,834,247 A * 11/1998 Comb et al. ............... 435/69.7

FOREIGN PATENT DOCUMENTS

WO          96/34878       * 11/1996

OTHER PUBLICATIONS

Dawson et al., Science vol. 266 (Nov. 1994) pp. 776–779.*
Dawson et al., JACS vol. 119, No. 19 (May 1997) pp. 4325–4329.*
Chong et al., Gene (Jun. 1997) pp. 271–281.*
Severinov et al., J. Biol. Chem. vol. 273, No. 26 (Jun. 26, 1998) pp. 16205–16209.*

* cited by examiner

Primary Examiner—Bennett Celsa
(74) Attorney, Agent, or Firm—Dann, Dorfman, Herrell & Skillman, P.C.

(57) ABSTRACT

The present invention provides a method of cleaving a recombinantly expressed protein from an intein and ligating the protein to a peptide containing an N-terminal cysteine having an unoxidized sulfhydryl side chain which comprises contacting the protein with the peptide in a reaction solution comprising a conjugated thiophenol, thereby forming a C-terminal thioester of the recombinant protein which spontaneously rearranges intramolecularly to form an amide bond linking the protein to the peptide. The present invention also provides a method of producing a protein-chip composition comprising the steps of: (a) contacting a solid support chip containing an amine group with a peptide containing an N-terminal cysteine having an unoxidized sulfhydryl side chain thereby covalently linking the peptide to the solid support, forming a peptide-chip; and (b) contacting a recombinant protein having an intein domain with the peptide-chip of step (a) with a reaction solution containing a conjugated thiophenol, thereby forming a C-terminal thioester of the recombinant protein which spontaneously rearranges intramoleculaly to form an amide bond covalently linking the protein to the peptide-chip, thereby producing a protein-chip composition.

10 Claims, 11 Drawing Sheets

1  2         1  2

A             B 1    2    3    4

SEQUENCE LISTING

<160> NUMBER OF SEQ ID NOS: 11

<210> SEQ ID NO 1
<211> LENGTH: 162
<212> TYPE: PRT
<213> ORGANISM: Artificial Sequence
<220> FEATURE:
<223> OTHER INFORMATION: Description of Artificial Sequence: generated
      by ligation of two proteins under certain conditions

<400> SEQUENCE: 1

Met Leu Phe Val Ala Leu Tyr Asp Phe Val Ala Ser Gly Asp Asn Thr
 1               5                  10                  15

Leu Ser Ile Thr Lys Gly Glu Lys Leu Arg Val Leu Gly Tyr Asn His
             20                  25                  30

Asn Gly Glu Trp Ala Glu Ala Gln Thr Lys Asn Gly Gln Gly Trp Val
         35                  40                  45

Pro Ser Asn Tyr Ile Thr Pro Val Gly Cys Leu Glu Lys His Ser Trp
     50                  55                  60

Tyr His Gly Pro Val Ser Arg Asn Ala Ala Glu Tyr Leu Leu Ser Ser
 65                  70                  75                  80

Gly Ile Asn Gly Ser Phe Leu Val Arg Glu Ser Glu Ser Ser Pro Gly
                 85                  90                  95

Gln Arg Ser Ile Ser Leu Arg Tyr Glu Gly Arg Val Tyr His Tyr Arg
            100                 105                 110

Ile Asn Thr Ala Ser Asp Gly Lys Leu Tyr Val Ser Ser Glu Ser Arg
        115                 120                 125

Phe Asn Thr Leu Ala Glu Leu Val His His His Ser Thr Val Ala Asp
    130                 135                 140

Gly Leu Ile Thr Thr Leu His Tyr Pro Ala Pro Lys Arg Gly Ile His
145                 150                 155                 160

Arg Asp

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Model
      peptide synthesized by solid phase peptide synthesis.
<221> NAME/KEY: SITE
<222> LOCATION: (11)
<223> OTHER INFORMATION: Xaa(position 11) is aminocaproate.
<223> OTHER INFORMATION: C-terminal K has a fluorescein moiety off the
      E-NH2 group.

<400> SEQUENCE: 2

```
Cys Glu Asp Asn Glu Tyr Thr Ala Arg Glu Xaa Lys
 1               5                  10
```

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Model
      peptide synthesized by solid phase peptide synthesis.
<221> NAME/KEY: SITE
<222> LOCATION: (11)
<223> OTHER INFORMATION: Xaa(position 11) is aminocaproate.

<400> SEQUENCE: 3

```
Cys Glu Asp Asn Glu Tyr Thr Ala Arg Glu Xaa Lys
 1               5                  10
```

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Model
      peptide synthesized by solid phase peptide synthesis.
<223> OTHER INFORMATION: K has a fluorescein moiety off the E-NH2 group;
      C-terminus is an amide group.

<400> SEQUENCE: 4

```
Cys Gly Arg Gly Arg Gly Arg Lys
 1               5
```

<210> SEQ ID NO 5
<211> LENGTH: 8
<212> TYPE: PRT
<213> ORGANISM: Unknown
<220> FEATURE:
<223> OTHER INFORMATION: Description of Unknown Organism: ligand

<400> SEQUENCE: 5

```
Pro Val Pro Tyr Glu Asn Val Gly
 1               5
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Model
      peptide synthesized by solid phase peptide synthesis.
<223> OTHER INFORMATION: C-terminus is an amide group.

<400> SEQUENCE: 6

```
Pro Pro Ala Tyr Pro Pro Pro Val Pro Lys
 1               5                  10
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
ccggtcatcg aaggtcgttg cctggagaaa cattcctggt at        42

<210> SEQ ID NO 8

```
-continued

<211> LENGTH: 41
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
catgatacca ggaatgtttc tccaggcaac gaccttcgat g                          41

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: motif
      within linker region

<400> SEQUENCE: 9

Ile Glu Gly Arg Cys
 1               5

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
ggatcccctg gtcatatgct ttttgtggca ctctatgatt ttgtg                      45

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
atgtttctcc aggctgttaa cggggtgat gtagttgctt gg                          42
```

METHODS OF LIGATING EXPRESSED PROTEINS

This application is a continuation of U.S. application Ser. No. 09/191,890, filed Nov. 13, 1998 (abandoned), which claims the benefit of U. S. Provisional Application No. 60/065,391, filed Nov. 13, 1997 and U.S. Provisional Application No. 60/093,990 filed Jul. 24, 1998.

This invention was made with the support of the Damon Runyon Scholars Award Program (P.A.C), the Irving A. Hansen Memorial Foundation (P. A. C.), the National Institutes of Health Grant No. R29-GM55843-01, R01-GM47021, F32-AI-09537and the Pew Scholars Program in the Biomedical Sciences, and the National Leukemia Research Association. The United States Government may have certain rights to this invention.

Throughout this application, various publications are referenced by number. Full citations for these publications may be found listed at the end of the specification and preceding the claims. The disclosures of these publications in their entireties are hereby incorporated by reference into this application in order to more fully describe the state of the art. A Sequence Listing is also provided.

FIELD OF THE INVENTION

The present invention relates to methods for chemically ligating two oligopeptides end to end with an amide bond, wherein at least one of the oligopeptides is a product of recombinant expression. Both oligopeptides may be recombinantly expressed products. The present invention further relates to segmental isotopic labeling of recombinant protein domains and uses thereof. The present invention also further relates to segmental expression of recombinant protein domains or subunits and subsequent ligation and uses thereof. The present invention also relates to use of these methods for producing protein-chip compositions and uses thereof.

BACKGROUND OF THE INVENTION

Recent years have seen the development of a number of methods designed to allow the incorporation of unnatural amino acids into proteins. These approaches include in vitro protein expression, site-specific protein modification and protein total synthesis. Although powerful, each of these techniques has associated with it certain practical or synthetic limitations which have to some extent restricted their widespread application. Total chemical synthesis, which provides unparalleled freedom to manipulate protein structure, has been dominated in recent years by the use of chemical ligation techniques (25–31). Among these, Kent's "native-chemical ligation" approach has proven a particularly powerful route to synthetic proteins (32). In this process, an N-terminal cysteine-containing peptide is chemically ligated to a peptide possessing a C-terminal thioester group with the resultant formation of a peptide bond at the ligation site. Despite the generality of the ligation chemistry, the strategy has been constrained by the need to generate the peptide building blocks using stepwise solid phase peptide synthesis (SPPS). The size limitations imposed by this requirement has restricted the application of native chemical ligation to the study of small proteins and protein domains.

Protein semi-synthesis, in which synthetic peptides and protein cleavage fragments are linked together, offers an attractive route to the generation of large protein analogs containing unnatural amino acids (33). The utility of existing semi-synthesis strategies is, however, tempered by the need to have unique chemical or enzymatic cleavage sites at the appropriate position within the protein of interest. A more general protein semi-synthesis approach in which synthetic peptides are directly chemically ligated to a recombinant protein without the need to carry out such initial fragmentation steps would be useful. Central to this strategy would be the ability to generate recombinant proteins bearing C-terminal α-thioesters, thereby facilitating the use of native chemical ligation.

The ability to alter protein structure and function by the insertion of unnatural amino acids has great potential to enhance our understanding of proteins, generate new tools for biomedical research, and create novel therapeutic agents. The current challenge was therefore to devise a method of generating the requisite α-thioester group in recombinant proteins.

Protein splicing, the process in which a protein undergoes an intramolecular rearrangement resulting in the extrusion of an internal sequence (intein) and the joining of the lateral sequences (exteins), has been shown to involve the intermediacy of a thioester (7, 8). A mutant version of the splicing protein has been demonstrated to be defective in completion of the splicing reaction but still capable of thioester intermediate formation (7, 8). The commercially available IMPACT™ (such as type vectors pCYB and pTYB vectors for $E.\ coli$ protein expression result in the generation of α-thioesters where a protein of interest can be expressed in frame fused with an intein-chitin binding domain (CBD) sequence (8). In the standard experiment, the protein of interest is cleaved from the intein-CBD with dithiothreitol or mercaptoethanol by a transthioesterification reaction while the chimera is bound to a chitin column.

Many large cellular and extracellular proteins are composed of independently folded protein modules with distinct biochemical properties of each, specific recombinations of which provide the overall functional character of the complete protein in vivo (1, 2). Consequently, there is interest in understanding the structural and functional interplay that occurs between such domains in the context of the multidomain protein. Experimentally, this can be achieved by manipulating the spatial and functional organization of the domains using standard recombinant DNA techniques. An alternative protein engineering strategy would involve the in vitro assembly of multidomain proteins from individual 'off-the-shelf' protein domains. Advantages include, the ability to prepare a large number of chimeric proteins from a small number of pre-made building-blocks, the ability to prepare fused proteins which are cytotoxic from individually expressed domains which are not, the potential incorporation of non-natural residues in an efficient combination of in vivo and chemosynthetic approaches, and the labeling of one segment of a protein for structural or biochemical investigation.

For a protein of length n residues, there is a limit of practicality for structure determination in solution by Nuclear Magnetic Resonance NMR spectroscopy (3). This is due to the loss of resolution of signals from both increased line widths at longer rotational correlation times, and from the increased number of signals of similar chemical shift overlapping with each other. Both effects are proportional to n.

Isotopic labeling can be used for the selection of coupled nuclei pairs, the perturbation of relaxation of complex or isochronous spin systems, and for the observation of low sensitivity nuclei (specifically $^{13}C$ and $^{15}N$). Its application to proteins is well exploited (e.g. (4, 5)). While early examples of highly tailored isotopic syntheses of peptides by chemical means (e.g. (6)) were useful, that approach was subsumed by the more general ability to uniformly label proteins by over-expression in isotopically substituted media. However, labeling, a segment of protein remains an important goal generally, and especially in connection with the study of multi-domain or modular proteins (e.g. (7, 8)). Labeling, a segment permits the assignment of that segment in a direct manner, because of the reduced spectral complexity. Moreover, in cases where the subdomains are individually folded, segmental labeling permits the structural determination of the independent segment, and possible comparison of the structure in isolated and multi-domain forms. Segmental labeling also permits simplified observation of the individual subdomain for spin relaxation, residual dipolar coupling analysis (9), or study of ligand binding by chemical shift perturbation/SAR-by NMR (10).

In principle, selectively labeled proteins can be obtained by joining labeled and unlabeled recombinant proteins together in vitro. Along these lines, Yamazaki et at exploited protein splicing in trans (11–13) to generate a segmentally labeled protein for NMR analysis (14). Using a genetically dissected protein splicing system, they were able to hook together labeled and unlabeled peptides derived from the α-subunit of *E. coli* RNA polymerase. Although elegant, this strategy resulted in the insertion of five unwanted amino acids at the splice junction, and required a chemical denaturation step. These features, alone, with the moderate yields often associated with the trans-splicing, process (11) reduces the general applicability of this approach.

Accordingly, ligation of native expressed recombinant proteins, protein domains and protein segments is therefore highly desirable as is domain and segmental protein labeling. Such applications are particularly useful in NMR.

The novel protein engineering, approach for expressed protein ligation described herein allows synthetic peptides to be chemically ligated to the C-terminus of recombinant proteins through a normal peptide bond (15, 16). Briefly, the recombinant protein to be ligated is first expressed as a N-terminal intein-CBD fusion, where the intein is a modified protein splicing element (17) and CBD is a chitin binding domain. Other affinity binding domains may be used. Following affinity purification on chitin beads, the immobilized fusion Protein is exposed to an aqueous Solution containing the synthetic peptide and a catalytic amount of thiophenol at pH 7.0. Under these conditions near quantitative ligation of the peptide to the protein is observed (15, 16). Expressed protein ligation is useful to generate semi-synthetic proteins (15, 16, 18), to facilitate two recombinant, folded proteins to be ligated together. Such an extension permits segmental isotopic labeling, and with multi-domain proteins for use in multidimensional NMR analysis. In addition, expressed protein ligation has uses in combinatorial chemistry with protein domains.

High throughput screening is a highly desirable and well-described approach for both diagnostic screening and for identification of novel, useful compounds for treatment of various ailments and diseases. High throughput screens require easy robotic manipulation, small sample size and rapid processing capabilities. Generally, such screens require binding of the sample to a solid phase support. One problem associated with such high-throughput systems is the tendency of the bound sample to diffuse in space with time unless physically delimited such as in Asample wells.@ Alternatively, rigorous washing conditions, necessary to ensure screening specificity tends to reduce or eliminate the screening signal. The protein chip compositions described herein solve this problem and provide a stable means for high-throughput diagnostic screening for the presence of proteins, antigens and antibodies. Moreover, the protein chip compositions described herein provide a means for introducing specific protein sequences which may include unnatural amino acids or analogs thereof. The availability of solid phase supports with amine groups available for peptide binding facilitates production of the protein chip compositions of the present invention comprising ligated expressed proteins produced by the novel methods described herein.

SUMMARY OF THE INVENTION

The present invention provides a method of cleaving a recombinantly expressed protein from an intein and ligating the protein to a peptide containing an N-terminal cysteine having an unoxidized sulfhydryl side chain which comprises contacting the protein with the peptide in a reaction solution comprising a conjugated thiophenol, thereby forming a C-terminal thioester of the recombinant protein which spontaneously rearranges intramolecularly to form an amide bond linking the protein to the peptide.

The present invention also provides a method of producing a protein-chip composition comprising the steps of: (a) contacting a solid support chip containing an amine group with a peptide containing an N-terminal cysteine having an unoxidized sulfhydryl side chain thereby covalently linking the peptide to the solid support, forming a peptide-chip; and (b) contacting a recombinant protein having an intein domain with the peptide-chip of step (a) with a reaction solution containing a conjugated thiophenol, thereby forming a C-terminal thioester of the recombinant protein which spontaneously rearranges intrameculaly to form an amide bond covalently linking the protein to the peptide-chip, thereby producing a protein-chip composition.

Accordingly, this invention relates to a method of ligating a recombinantly expressed protein to an oligopeptide. Utilizing a particular reagent, i.e., a thiophenol, to cleave the recombinantly expressed protein from its manufacturing process, and in the presence of the oligopeptide to which it is to be ligated, the desired ligation reaction occurs without the necessity for conversion to the necessary α-thioester prior to ligation with the oligopeptide. One aspect of the instant invention provides a one-pot, synthetic procedure for ligating a recombinantly expressed protein to a peptide.

The present invention further provides a method of generating a recombinant protein alkyl thioester derivative comprising cleaving a recombinant protein having an intein in a reaction solution containing an alkyl thiol, thereby generating the recombinant protein alkyl thioester derivative.

Another aspect of this invention, is a method of ligating the recombinant protein alkyl thioester derivative to a peptide containing an N-terminal cysteine comprising contacting the protein with the peptide with a reaction solution containing a conjugated thiophenol, which spontaneously rearranges intramolecularly to form an amide bond linking the protein to the peptide.

Still another aspect of this invention further relates to a method for producing a protein chip composition comprising a solid support covalently bound to an oligopeptide which is ligated to a recombinantly expressed protein. This invention also relates to protein chip compositions produced by this method.

A still further aspect of the present invention relates to a method for diagnostic screening for a specific protein, antibody or antigen using the protein-chip composition. This invention also relates to diagnostic kits comprising the protein-chip composition of the present invention.

In accordance with yet another aspect of this invention, there is provided a method for the preparation of semi-synthetic proteins of any size.

It is an object of the present invention to chemical ligate a synthetic peptide to a recombinant protein.

It is a still further object of the instant invention to generate a recombinant protein possessing the necessary reactive thioester moiety at its C-terminus so as to provide a facile means of ligating the recombinant protein to the desired peptide.

It is also an object of the present invention to prepare semi-synthetic versions of the various proteins, especially those which are subunits of E. coli RNA polymerase, by ligating the expressed protein to a synthetic peptide.

It is a still further object of the present invention to provide a method of systematically chemically modifying the C-terminal region of a recombinantly expressed protein.

It is yet a still further object of the present invention to provide a method for the preparation of the protein chip composition.

It is also a further object of the present invention to provide a method of systematically chemically modifying the protein chip composition.

It is still another object of the present invention to provide a diagnostic kit comprising the protein chip composition.

It is yet another further object of the present invention to provide a method for diagnosing disease using the protein chip composition of this invention.

It is another object of this invention to provide a method for identifying proteins, antigens or antibodies using the protein chip composition of this invention.

It is yet a still further object of the present invention to provide a method of ligating together two recombinant proteins.

It is also a further object of the present invention to provide a method for NMR spectroscopy using proteins segmentally labeled by the provided method.

It is still further an object of the present invention to provide a method of segmentally labeling a protein.

Finally, it is also an object of the present invention to provide a method of generating a cytotoxic recombinant protein by ligating together the non-cytotoxic segments of the protein.

BRIEF DESCRIPTION OF THE DRAWINGS

FIGS. 1–1B. is a diagram showing the phosphotyrosine tails in Src and Csk. In FIG. 1B, the diagram shows that Csk is highly homologous to Src but lacks a C-terminal tyrosine-containing tail. Proposed ligation of a phosphotyrosine tail might lead to a conformational change like that found in Src.

FIG. 2B shows a Coomassie stained SDSPAGE gel of $Csk^{PEP}$ crude reaction product mixture. Lane 1: Molecular weight markers from the top, 97 kDa, 66 kDa, 45 kDa, 31 kDa, 21.5 kDa; Lane 2: wild type Csk Lane 3: $Csk^{PEP}$ crude ligation product mixture, bands at 56 kDa and 69 kDa presumed to be GroEL and DnaK. Lane 4: Co-mixture of wild type Csk and $Csk^{PEP}$ crude ligation product mixture.

FIG. 2C shows the characterization of semi-synthetic proteins by electrospray mass spectrometry. Top panel: full-length wild type Csk, expected mass=50,705 Da (average isotope). Middle panel: $Csk^{PEP}$, expected mass= 52,540 Da (average isotope). Bottom panel: $Csk^{pPEP}$, expected mass=52,619 Da (average isotope). Each sample was isolated by reverse-phase HPLC and mass analyzed using a P.E.-Sciex API-100 mass spectrometer. Predicted masses were calculated using the program MacBioSpec. Note, the ligated Csk products were engineered to have the sequence Pro-Gly added to their C-termini, and Edman sequencing indicated that the N-terminal methionine had been removed from the Csk expressed in the pCBY2 vector. That the ligation products contained only one N-terminus (i.e., from Csk) combined with the MS data provides unambiguous characterization of the semi-synthetic proteins.

FIG. 3A shows the non-denaturing PAGE of $Csk^{PEP}$ and $Csk^{pPEP}$. Lane 1: $Csk^{PEP}$; Lane 2: $Csk^{pPEP}$ Proteins are visualized with fluorescence imaging (Storm, Molecular Dynamics). The minor, faster migrating bands in both lanes are presumed to represent proteolytic degradation products. FIG. 3B shows the non-denaturing PAGE of the Src family member Lck (aa 64–509, K273R) in its unphosphorylated and tail-phosphorylated form. Proteins were prepared and characterized previously (27). Lane 1: unphosphorylated Lck; Lane 2: 505-phosphorylated Lck. Proteins are imaged with Coomassie staining.

In FIG. 5B full-length $\sigma^{70}$, $\sigma^{lig}$, $\sigma^{cleav}$ support promoter-dependant transcription by $E.\ coli$ RNA polymerase core and the indicated $\sigma$ proteins, and abortive initiation reaction was performed on the gal P1 promoter in the presence of 0.5 mM ApU and 50 $\mu$M $\alpha$-[$^{32}$P]CTP (30 Ci/mmol). Reaction proceeded for 15 minutes at 37° C., and reaction products were resolved by PAGE. An autoradiogram of a 20% urea-gel is presented. FIG. 5C shows full-length $\sigma^{70}$ and $\sigma^{lig}$, but not $\sigma^{cleav}$ support promoter-dependant transcription by $E.\ coli$ RNA polymerase core on a –10/–35 type promoter. RNA polymerase holoenzyme was reconstituted as in FIG. B, and abortive initiation reaction was performed on the T7 A2 promoter in the presence of 0.5 mM CpG and 50 $\mu$M $\alpha$-[$^{32}$P]CTP (30 Ci/mmol). Reaction products were resolved analyzed as in FIG. B.

FIG. 7A. Analytical reverse phase HPLC profile of the crude ligation mixture after 90 hours reaction. A linear gradient of 32–46% B (B=90:1 CH$_3$CN:H$_2$O, 0.1% TFA) over 30 minutes was used. ESMS was used to identify the various components in the mixture which Vale labeled accordingly. The Abl SH3 domain is converted to the more reactive benzyl and phenyl thioester derivatives in situ. FIG. 7B Electrospray mass spectrum (mass reconstruction) of the purified product, Abl[G$^{120}$C$^{121}$][SH2-$^{15}$N]SH(32); expected mass (av. isotope comp.)=18, 240.2 Da. ESMS was performed on a Perkin-Elmer-Sciex (Thornhill, ON, Canada) API-100 mass spectrometer. Predicted masses were calculated using the program MACBIO-MASS (S. Verumi and T. Lee, City of Hope, Duarte, Calif.).

FIG. 8C. S$^{121}$ in the wildtype is ligated to C$^{121}$ in the segment labeled material. In FIG. 8C–8E, the wildtype subspectrum is shown in solid lines, and the segment labeled protein in clashed lines. FIG. 8D. Residue G$^{130}$, shows a small $^1$H chemical shift, and does FIG. 8E. A$^{196}$. Both these residues are spatially close to the junction between SH3 and SH2 and presumably are slightly structurally perturbed.

DETAILED DESCRIPTION OF THE INVENTION

Figure 1A:
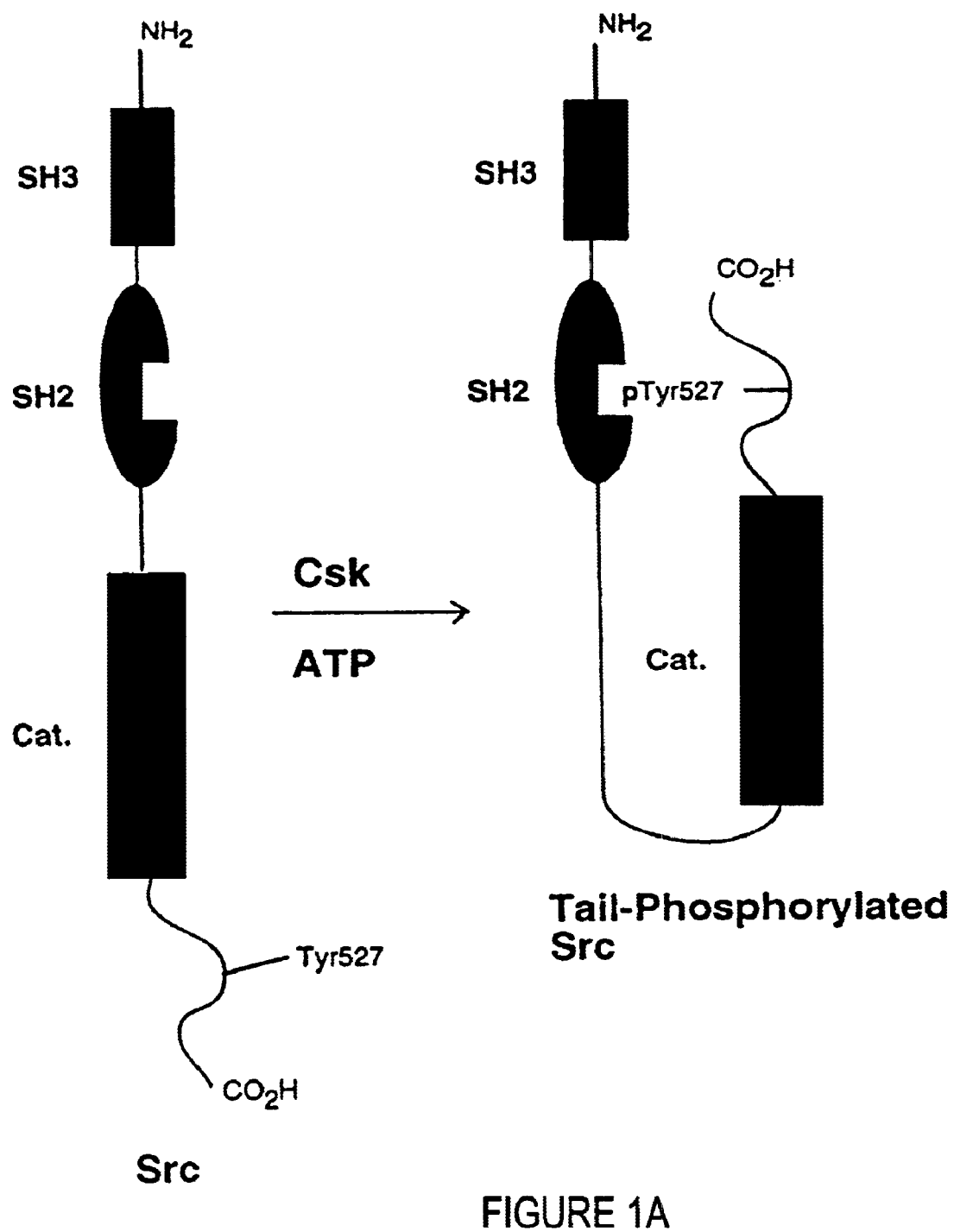
In FIG. 1A, the diagram shows that the phosphorylation of the Src tail on tyrosine is catalyzed by Csk. This phosphorylation results in a conformational change involving an intramolecular interaction between the Src tail and the SH2 domain.

The present invention provides a method of producing a protein-chip composition comprising the steps of: (a) contacting a solid support chip containing an amine group with a peptide containing an N-terminal cysteine having an unoxidized sulfhydryl side chain thereby covalently linking the peptide to the solid support, forming a peptide-chip; and (b) contacting a recombinant-intein protein, with the peptide-chip of step (a) in a reaction solution containing a conjugated thiophenol, thereby cleaving the intein domain from the recombinant protein, thereby forming a C-terminal thioester of the recombinant protein which spontaneously rearranges intramoleculaly to form an amide bond covalently ligating the protein to the peptide-chip, thereby producing a protein-chip composition.

The present invention further provides a method of producing a protein-chip composition comprising the steps of: (a) contacting a solid support chip containing an amine group with a peptide containing an N-terminal cysteine having an unoxidized sulfhydryl side chain thereby covalently linking the peptide to the solid support, forming a peptide-chip; (b) generating a recombinant protein alkyl thioester derivative comprising contacting a recombinant protein having an intein in a reaction solution containing an alkyl thiol, thereby generating the recombinant protein alkyl thioester derivative; and (c) ligating the recombinant protein alkyl thioester derivative of step (b) with the peptide-chip of step (a) in a reaction solution containing a conjugated thiophenol, thereby which spontaneously rearranges intramoleculaly to form an amide bond covalently linking the protein to the peptide-chip, thereby producing a protein-chip composition.

According to one embodiment of this invention, the recombinantly expressed protein is expressed from an intein-chitin binding domain (CBD) expression vector. Other affinity binding domains, well-known in the art are also contemplated by the present invention. According to another embodiment of this invention, the cleavage and ligation occurs simultaneously. According to another embodiment of the present invention, the conjugated thiophenol is selected from the group consisting of thiophenol, 1-thio-2-nitrophenol, 2-thiobenzoic acid, 2-thiopyridine, 4 thio-2-pyridine carboxylic acid and 4-thio-2-nitropyridine. Yet another embodiment of the present invention is the reaction solution further comprising benzyl mercaptan. In yet still another embodiment of the present invention, the reaction solution comprises an alkyl thiol. According to an embodiment of this invention, the alkyl thiol is an ethanethiol. According to yet another embodiment of the present invention the thioester formed is an alkyl thioester. Still, according to another embodiment of this invention, the alkyl thioester is an ethyl thioester. Also another embodiment of the present invention is wherein the alkyl thioester is isolated prior to ligation. Yet another embodiment of this invention is wherein the thioester is isolated prior to ligation.

According to another embodiment of the present invention, the peptide is a recombinantly expressed protein. An embodiment of this invention is wherein the recombinantly expressed protein is labeled with a detectable marker. In an embodiment of this invention, the detectable marker is selected from the group consisting of a radiolabeled molecule, a fluorescent molecule, an enzyme, a ligand, a photo chemical cross-linker, a nuclear isotope and a magnetic bead. According to still another embodiment of the present invention, the conjugated thiophenol is thiophenol. According to one embodiment of the present invention the reaction is conducted at about pH 7. According to another embodiment of the present invention, the reaction is conducted at about pH 6. According to still another embodiment of the present invention, the reaction is conducted in a buffered solution. Also an embodiment of the present invention is wherein the recombinant protein is expressed by a pTYB expression plasmid. According to another embodiment of the present invention, the recombinant protein is a segment thereof. According to still another embodiment of the present invention, the exposure is for about approximately 5 minutes to overnight. Yet still another embodiment of the present invention is wherein the recombinant protein is folded. According to one embodiment of this invention, the protein segment is a protein domain. According to still another embodiment of this invention, the domain concentration is about 0.5 mM. According to yet still another embodiment of this present invention the domain is in molar excess.

According to another embodiment of the present invention, the recombinant protein is a non-cytotoxic segment of a cytotoxic protein. Still another embodiment of this invention is a method for generating a cytotoxic recombinant protein. According to yet still another embodiment of the present invention, the recombinant protein is partially labeled with a detectable marker. Another embodiment of this invention is a method for generating a recombinant protein partially labeled with a detectable marker. The present invention also provides a method for generating a recombinant protein partially labeled with a detectable marker comprising: (a) fragmenting the recombinant protein, thereby generating protein segments; (b) separating the protein segments generated in step (a); (c) labeling with a detectable marker a portion of the separated protein segments generated in step (b), thereby generating a at least one labeled protein segment and at least one unlabeled protein segment; and (c) ligating by the method provided herein, the labeled protein segment to the unlabeled protein segment, thereby generating a recombinant protein partially labeled with a detectable marker. According to an embodiment of this invention, the separating of step (b) is selected from the group consisting of size separation and charge separation. According to another embodiment of this invention, the separating of step (b) is by gel electrophoresis. According to still another embodiment of this invention, the separating of step (b) is by chromatography. According to yet still another embodiment of the present invention, the recombinant protein is labeled with a detectable marker prior to the fragmenting of step (a). According to still yet another embodiment of the present invention, step (d) comprises ligating by the provided method, the labeled recombinant protein to an unlabeled peptide.

The present invention also contemplates use of the methods and compositions of the present invention in Nuclear Magnetic Resonance comprising using a recombinant protein partially labeled by the method provided herein. According to an embodiment of this invention, the detectable marker is selected from the group consisting of a radiolabeled molecule, a fluorescent molecule, an enzyme, a ligand, a photochemical cross-linker, a nuclear isotope and a magnetic bead.

The present invention also contemplates a method for generating a recombinant protein comprising: (a) expressing a recombinant protein segment; (b) expressing a second recombinant protein segment; and (c) ligating the recombinant protein segment to the second recombinant protein segment by the method provided herein, thereby generating the recombinant protein.

According to an embodiment of the present invention, the recombinant protein segment is expressed by a pTYB, a pCYB, a pKYB, a pMYB, or other IMPACT™-type vector expression plasmid. According to still another embodiment of this invention, the recombinantly expressed protein is labeled with a detectable marker. According to an embodiment of this invention, the detectable marker is selected from the group consisting of a radiolabeled molecule, a fluorescent molecule, an enzyme, a ligand, a photochemical cross-linker, a nuclear isotope and a magnetic bead.

The present invention further contemplates a method for generating a cytotoxic recombinant protein comprising: (a) expressing a non-cytotoxic recombinant protein segment; (b) expressing a non-cytotoxic second recombinant protein segment; and (c) ligating the non-cytotoxic recombinant protein segment to the second recombinant protein segment by the method provided herein, thereby generating the cytotoxic recombinant protein.

The present invention also contemplates a method for generating a recombinant protein partially labeled with a detectable marker comprising: (a) expressing a protein segment; (b) labeling the protein segment; and (c) ligating by the method provided herein, the protein segment to a second protein segment thereby generating the recombinant protein partially labeled with a detectable marker. An embodiment of this invention is a method for generating a recombinant protein partially labeled with a detectable marker comprising: (a) expressing a protein segment; and (b) ligating by the provided method, the protein segment to a second protein segment, previously labeled with a detectable marker, thereby generating a partially labeled recombinant protein.

Still further, the present invention contemplates a method for generating a recombinant protein partially labeled with a detectable marker comprising: (a) fragmenting the recombinant protein, thereby generating protein segments; (b) separating the protein segments generated in step (a); (c) labeling with a detectable marker a portion of the separated protein segments generated in step (b), thereby generating a at least one labeled protein segment and at least one unlabeled protein segment; and (d) ligating by the method provided herein, the labeled protein segment to the unlabeled protein segment, thereby generating a recombinant protein partially labeled with a detectable marker.

According to an embodiment of this invention, the fragmentation of step (a) is by proteolysis. According to another embodiment of this invention, the framentation is by chemical cleavage or by physical disruption such as aspiration or sonication. According to another embodiment of this invention, the separating of step (b) is selected from the group consisting of size separation and charge separation. According to still another embodiment of this invention, the separating of step (b) is by gel electrophoresis. According to yet another embodiment of this invention, the separating of step (b) is by chromatography. According to yet still another embodiment of this invention, the detectable marker of step (c) is selected from the group consisting of a radiolabeled molecule, a fluorescent molecule, an enzyme, a ligand, a photochemical cross-linker, a nuclear isotope and a magnetic bead. Yet according to still another embodiment of this invention, the recombinant protein is labeled with a detectable marker prior to the fragmenting of step (a). According to an embodiment of this invention, step (d) comprises ligating by the method provided herein, the labeled recombinant protein to an unlabeled peptide. According to another embodiment of this invention, step (d) comprises ligating by the method provided herein, the unlabeled recombinant protein to the labeled peptide.

According to another embodiment of this invention, the solid support chip is selected from the group consisting of silicon, glass, polypropylene, polystyrene, cellulose, plastic and paper. According to yet another embodiment of this invention, the solid support chip provides at least one substantially flat surface. Still, according to another embodiment of the present invention, the spatial orientation of the peptides on the surface of the solid support chip forms an array. According to still another embodiment of this invention, the peptide comprises a single cysteine residue or analog thereof. Also, according to another embodiment of this invention, the peptide comprises a non-natural amino acid residue. Additionally, according to another embodiment of this invention, the protein comprises an antibody or portion thereof. According to an additional embodiment of this invention, the protein comprises an antigen.

In addition, the present invention provides a protein-chip composition produced by the above-described method.

The present invention also provides a method of identifying the presence of a protein in a sample which specifically binds a protein chip protein comprising the steps of: (a) contacting the sample with the provided protein-chip composition under conditions permissive to the formation of a complex between the protein and the protein-chip composition; (b) measuring the amount of complex formed, thereby determining the amount of protein present in the sample; and (c) comparing the amount of protein in the sample with the amount determined for a control sample known to be free of the protein, the presence of a complex formed indicating the presence of a protein binding protein in the sample. One embodiment of this invention is step (a) further comprising contacting the complex with a detecting antibody. Another embodiment of this invention is step (a) further comprising washing the complex under conditions to substantially reduce non-specific complex formation. According to still another embodiment of this invention, the protein in the sample is an antibody specific for the protein chip protein. According to yet another embodiment of this invention, the protein in the sample is an antigen. Further, according to an embodiment of this invention, the antigen is selected from the group consisting of a tumor-associated antigen, a cell-specific antigen, a tissue-specific antigen, an enzyme, a nucleic acid, an immunoglobulin, a toxin, a viral antigen, a bacterial antigen and a eukaryotic antigen. Further still, according to an embodiment of this invention, the antigen is selected from the group consisting of a mammalian, insect and E. coli antigen. Still further, according to an embodiment of this invention, the protein chip protein is an antibody specific for an antigen. Yet further still, according to an embodiment of this invention, the protein chip protein is an antigen. In yet another embodiment of this invention the antigen is selected from the group consisting of a tumor-associated antigen, a cell-specific antigen, a tissue-specific antigen, an enzyme, a nucleic acid, an immunoglobulin, a toxin, a viral antigen, a bacterial antigen and a eukaryotic antigen. Still in yet a further embodiment of this invention, the protein chip protein is an antigen selected from the group consisting of a mammalian, insect and E. coli antigen.

The present invention further provides a diagnostic kit for identifying the presence of an antigen in a sample comprising: (a) the provided protein-chip, wherein the protein-chip comprises an antibody specific for the antigen; and (b) reagents facilitating the formation of a complex between the antibody and the antigen in the sample. One embodiment of this invention, is further comprising a detecting antibody capable of binding the antigen. According to another embodiment of this invention, the detecting antibody is labeled with a detectable marker. According to yet another embodiment of this invention, the detectable marker is selected from the group consisting of a radioactive isotope, enzyme, a photochemical cross-linker, a nuclear isotope, magnetic bead, dye, flourescent marker and biotin.

The present invention further still provides a diagnostic kit for identifying the presence of an antibody in a sample comprising: (a) the provided protein-chip, wherein the protein-chip comprises an antigen capable of being specifically bound by the antibody; and (b) reagents facilitating the formation of a complex between the antibody and the antigen in the sample. One embodiment of this invention is further comprising a detecting antibody capable of binding the antibody in the sample. According to another embodiment of this invention, the detecting antibody is labeled with a detectable marker. According to yet another embodiment of this invention, the detectable marker is selected from the group consisting of a radioactive isotope, enzyme, a photochemical cross-linker, a nuclear isotope, magnetic bead, dye, flourescent marker and biotin.

The present invention additionally provides a diagnostic kit for identifying the presence of a target protein in a sample comprising: (a) the provided protein-chip, wherein the protein-chip comprises an protein capable of specifically binding the target protein; and (b) reagents facilitating the formation of a complex between the protein and the target protein in the sample. One embodiment of this invention is further comprising a detecting antibody capable of binding the target protein. According to another embodiment of this invention, the detecting antibody is labeled with a detectable marker. According to yet another embodiment of this invention, the detectable marker is selected from the group consisting of a radioactive isotope, enzyme, magnetic bead, dye, flourescent marker and biotin.

The present invention contemplates the reusability of the protein chip composition following screening.

The invention described herein eliminates the need for an elaborate protecting group strategy since the protein-thioester moiety is generated in situ. This precursor thioacid (protein-α-COSH) is recombinantly expressed by a standard technique using solid-phase peptide resin supports.

The conditions stated above, permit the formation of an unprotected protein which is equipped with the activated thioester. Subsequent reaction with a second peptide containing a terminal cysteine residue permits a facile coupling with the formation of a native peptide bond, and thus generates oligopeptide chains of 100 or more amino acid residues. This provides a convenient way of adding an unnatural peptide sequence to a portion of a naturally occurring protein.

The ligation method of the present invention combines the formation of a native peptide bond at the ligation site with the advantages of chemoselective reaction of unprotected peptides. This second generation ligation chemistry dramatically increases the size of native backbone polypeptides directly accessible by total chemical synthesis. It can be usefully applied to a wide range of synthetic targets, including proteins of moderate size, and it allows direct access to protein functional domains. Native chemical ligation is a foundation stone of a general modular approach to the total chemical synthesis of proteins. Furthermore, it is compatible with the use of both chemically synthesized peptides and peptide segments derived from other sources.

Straightforward total chemical synthesis of proteins represents the realization of an important objective of organic chemistry. It provides for unrestricted variation of protein covalent structure made possible by general synthetic access, and provides new impetus to exploration of the structural basis of properties such as folding, stability, catalytic activity, binding, and biological action.

The thiophenol utilized in the present invention may be substituted or unsubstituted, with thiophenol itself being preferred due to its commercial availability and reaction characteristics. Other equivalents are conjugated thiols such as 1-thio-2-nitrophenol, 2-thiobenzoic acid, 2-thiopyridine, ethanethiol is a preferred reactant. 4 thio-2-pyridine carboxylic acid and 4-thio-2-nitropyridine.

The protein utilized as a component of the instant reaction is typically available from protein splicing, in which a protein undergoes a series of chemical rearrangements culminating in the excision of an internal sequence (intein) with concomitant joining of the lateral sequences (exteins), has been shown to involve the intermediacy of a thioester (7). The commercially available IMPACT™ type expression plasmids (New England Biolabs) (e.g. pCYB, pTYB) employ a engineered intein genetically fused to the C-terminus of a protein of interest (38). Rational mutations in the intein component prevent protein splicing from going to completion, although the initial chemical rearrangements involving the generation of thioesters can still take place. Following affinity purification of the chimeric protein (via a chitin binding domain (CBD) placed downstream of the intein) the protein of interest is released from the immobilized chimera by treatment with dithiothreitol. It was postulated that it would be possible to manipulate this system in order to generate the necessary reactive thioesters central to the semi-synthetic strategy of the present invention.

Figure 1B:
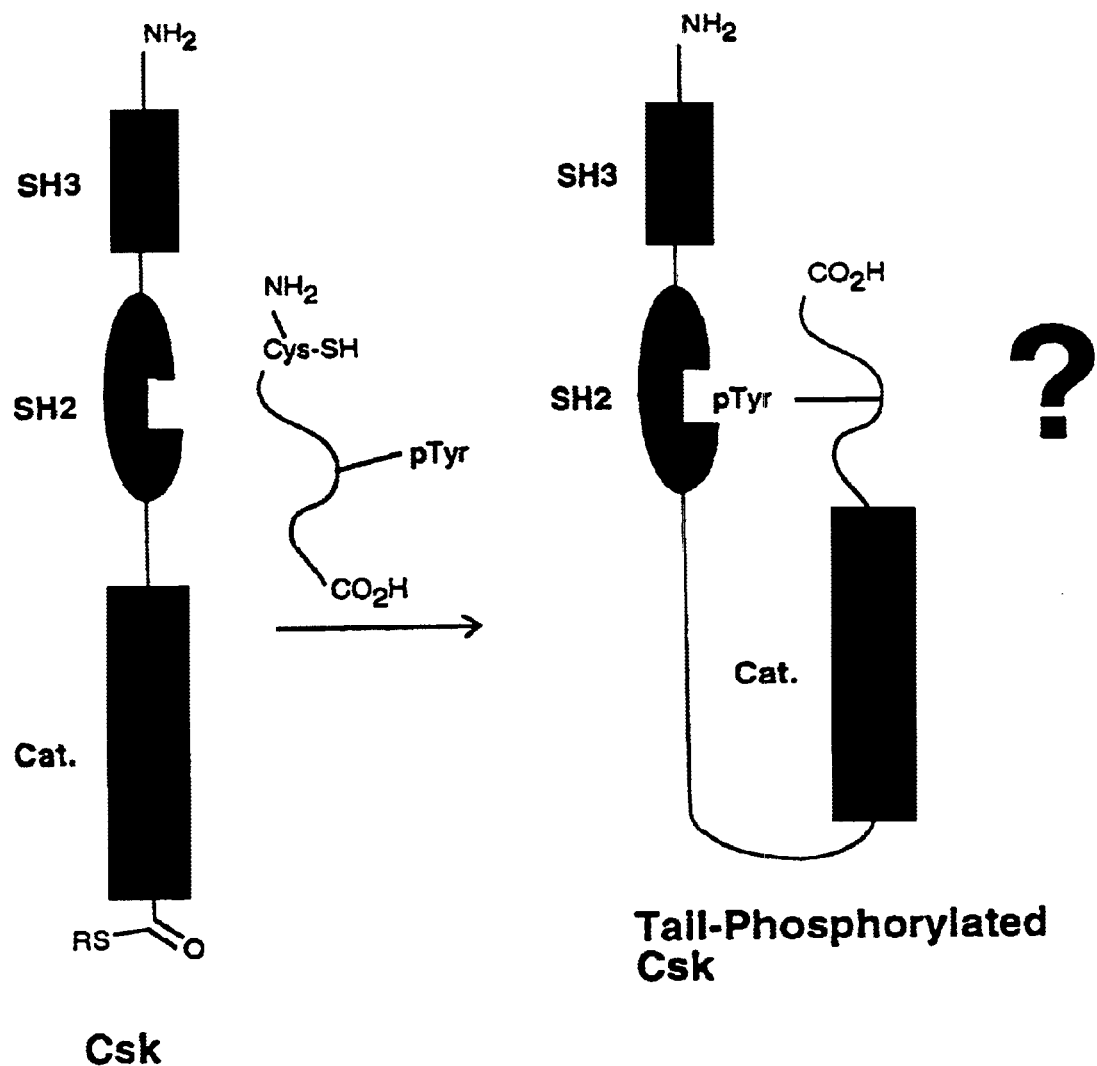

As applications of the method of the present invention, the semi-synthesis of C-terminal Src kinase (Csk) modified proteins and a 600 amino acid long derivative of the *E. coli* RNA polymerase $\sigma^{70}$ subunit were investigated. Csk-catalyzed phosphorylation of a highly conserved C-terminal tail tyrosine of Src family members results in an intramolecular interaction between the SH2 domain and the C-terminal phosphotyrosine (FIG. 1A) (9–14). Csk, a 50 kDa protein, is 40–50% identical in amino acid sequence to Src family members (15, 16) but lacks a C-terminal tyrosine-containing tail (FIG. 1) (9, 10). In particular, the addition of a phosphotyrosine tail to Csk and determining the potential conformational effects (FIG. 1B) was studied. Although extending the Csk C-terminus could in principle be carried out using recombinant methods (17), there would be no way of assuring specific C-terminal phosphorylation of an engineered tyrosine by chemical or enzymatic methods. In fact, attempts at simply adding a nine amino acid tyrosine-containing tail to wild type Csk led to very poor protein expression using standard recombinant methods (18). Furthermore, none of the existing protein engineering techniques appeared to be suitable for the generation of this large and complex protein.

The approach of the present invention (i.e., 'expressed protein ligation') effectively unites the fields of synthetic peptide chemistry and recombinant protein biotechnology. In doing so, it facilitates systematic chemical investigation of proteins to the same level previously restricted to the study of small bioactive peptides. N-terminal methionine deletion which has been observed in the several cases using the intein expression vector creates the possibility for ligation of peptides or proteins to an N-terminal cysteine (placed at the second codon of the recombinant protein) (24). This expands the utility of expressed protein ligation as a means of inserting unnatural or isotopically labeled amino acids in the middle as well as at the ends of recombinant proteins.

The feasibility of the semi-synthetic approach of the present invention was first explored in a series of model studies. As a test system, a short recombinant fragment corresponding to amino acids 500–567 of the 613 amino acid-long *E. coli* RNA polymerase $\sigma^{70}$ subunit was genetically fused to the intein-CBD, overexpressed and purified by affinity chromatography on chitin beads. Exposure of immobilized intein-fusion constructs to free cysteine has been shown to induce cleavage (38), and indeed this was confirmed in the present system. It was then evaluated whether the immobilized construct could be chemically ligated to a short synthetic peptide ($NH_2$-Cys-Glu-Asp-Asn-Glu-Tyr-Thr-Ala-Arg-Glu-aminocaproate-Lys-ε-[fluoroscein]-$CO_2H$; SEQ ID NO: 2) containing an N-terminal cysteine to facilitate ligation and a C-terminal fluorescein reporter group. Initial studies in which the beads were simply treated with a solution containing 1 mM peptide at pH 7.3 were unsuccessful and neither ligation nor protein cleavage was detected, even after prolonged incubations.

The presence of thiol co-factors can appreciably accelerate native chemical ligation reactions both in solution (24) and on solid-phase. Consequently, the effect of several thiol co-factors was investigated on our model ligation/cleavage reaction N-acetyl cysteine was the only co-factor which failed to support both the cleavage and the ligation reactions. DTT, cysteine and mercaptoacetic acid caused efficient cleavage of the chimeric protein but did not support ligation. Reverse-phase HPLC revealed that all cleavage reactions contained two main peaks. Electrospray mass spectrometry (ESMS) indicated that the first HPLC peak (~75% of the total product) corresponded to σ amino acids 501–567 (e. g., the first methionine residue was removed). The second, minor peak contained the unprocessed product with the first methionine in place. The products of the cysteine- and mercaptoacetic acid cleavages had masses consistent with the expected C-terminally modified polypeptides, whereas the product of DTT cleavage consistently gave a mass of ~72 Da higher than the expected product with a free C-terminal carboxyl (39). The origin of this mass discrepancy is unknown.

Surprisingly, thiophenol was found to be the only co-factor tested that supported both efficient cleavage and efficient ligation. Cleavage with thiophenol gave a major product with a mass corresponding to the phenyl α thioester derivative of the sigma polypeptide. Exposure of this material to elevated pH resulted in the loss of 92 Da, consistent with the hydrolysis of the thioester to the free acid. Inclusion of 2% v/v of thiophenol in the ligation cocktail at pH 7.3 containing the synthetic peptide (1–2 mM) resulted in extremely efficient ligation (>90% after overnight incubation) as indicated by HPLC and ESMS analysis. The ligation product had a mass of 9022 Da, and thus corresponded to the desired semi-synthetic polypeptide [expected mass=9023 Da since the masses of σ fragment and synthetic peptide were 7214 Da and 1827 Da, respectively]. Significantly, the thiophenol supported cleavage and ligation reactions; both took several hours to go to completion. The slow kinetics of cleavage/ligation probably reflects the position of the equilibrium in the initial N S acyl transfer within the chimera. Based on these observations, the ligation mechanism shown in FIG. 2A in which the highly reactive phenyl $^\alpha$thioester derivative of the recombinant polypeptide is produced in situ during the ligation process. Once generated, this derivative quickly and irreversibly reacts with the synthetic peptide to give the final product, thus generating a reaction sink.

It was next investigated whether a functional semisynthetic $\sigma^{70}$ could be obtained by expressed protein ligation. Genetic and biochemical data indicate that in the context of bacterial RNA polymerase holoenzyme, protein-DNA contacts between the evolutionary conserved, C-terminal region 4.2 of $\sigma^{70}$ and the −35 promoter element are crucial for promoter recognition (40, 41). In addition, protein-protein contacts between σ region 4.2 and transcription factors are crucial for transcription activation (26, 27). Thus, efforts were focused on the semi-synthesis of a $\sigma^{70}$ analog containing a chemically synthesized region 4.2. A recombinant protein containing the first 567 amino acids of $\sigma^{70}$ fused to intein-CBD was used in the ligation reaction. This fragment was chosen because the region of $\sigma^{70}$ defined by residues 560–570 is evolutionary variable in length and sequence (44) and is likely to tolerate a non-natural cysteine introduced as a result of ligation. Sequence comparisons also indicate that region 4.2 does not extend past $\sigma^{70}$ His$^{600}$ on the C-terminal side (44). Based on this data, a 34 residue peptide was synthesized which corresponded to amino acids 568–600 of $\sigma^{70}$ with an additional cysteine residue at the N-terminus to promote ligation. Chemical ligation of the synthetic 34-mer to the 567 residue recombinant protein was carried out using the general conditions described above. As a control, a second reaction was performed in the absence of the synthetic peptide, and thus should have contained the cleavage product only. Analysis of the crude reaction mixtures by SDS PAGE showed the presence of the expected ~70 KDa and ~65 KDa bands in the ligation and control reactions respectively (lanes 8 and 14 in FIG. 5A). As in the model studies, the crude ligation reaction was essentially free of unligated material. although the mixture did contain a contaminant band at around 55 KDa (labeled $\sigma^x$ on FIG. 5A).

Figure 5:
FIGS. 5A–5C. shows the binding of full-length $\sigma^{70}$ and the ligation product ($\sigma^{lig}$), but not the cleavage product ($\sigma^{cleav}$), to immobilized $AsiA_{HIS}$ by the $Ni^{2+}$-co-immobilization assay. The indicated proteins were loaded onto $Ni^{2+}$-NTA-agarose beads (L) and the unbound protein was removed (F). The beads were extensively washed and the bound protein was eluted with buffer containing 100 mM imidazole (E). The protein fractions were analyzed by SDS-PAGE on a 8–25% Phast-gel (Pharmacia). A contaminating band ($\sigma^x$) in the cleavage and ligation products lanes results from an uncharacterized protelotytic event during ligation/cleavage reactions and does not associate with AsiA$_{HIS}$ (lanes 11 and 12).

The bacteriophage T4 antisigma protein, AsiA, engineered with a C-terminal hexahistidine tag was used in a Ni$^{2+}$-NTA agarose co-immobilization assay to investigate the binding of the ligation product, the cleavage product, and the full-length recombinant $\sigma^{70}$ to AsiA (FIG. 5A). A mixture of AsiA$_{His}$ and recombinant $\sigma^{70}$ was loaded onto Ni$^{2+}$-NTA agarose beads (lane 4) and the unbound material removed (lane 5). The beads were subsequently washed with 10 mM imidazole buffer and then eluted with 100 mM imidazole buffer. Both $\sigma^{70}$ and AsiA$_{His}$ were found in eluted fraction (lane 6). Since recombinant $\sigma^{70}$ in the absence of AsiA$_{His}$ did not interact with the beads (lane 3), we conclude that $\sigma^{70}$ was retained on the beads through direct protein-protein interaction with AsiA$_{His}$, as expected (37). When a mixture of AsiA$_{His}$ and the cleavage product, containing the first 567 amino acids of $\sigma^{70}$, was loaded onto Ni$^{2+}$-NTA agarose beads (lane 7), all of the $\sigma^{70}$ fragment appeared in the unbound fraction (lane 8), whereas an analogous experiment with the ligation product indicated interaction of the semisynthetic 600 amino acid-long $\sigma^{70}$ derivative with AsiA$_{His}$ (lane 12). In the absence of AsiA$_{His}$, semisynthetic $\sigma^{70}$ did not interact with the Ni$^{2+}$-NTA agarose beads (lane 15).

The crude cleavage and ligation reactions each contain an additional protein (labeled $\sigma^x$ on FIG. 5A) that migrates faster than either the expected cleavage or ligation products. The appearance of this band is dependent on the addition of σ-intein overproducing lysates to the chitin beads, and we conclude that this band is probably a product of σ proteolysis. As this a fragment may interfere with the function of the desired ligation product, it was removed using the AsiA immobilization method described above (since $\sigma^x$ did not bind to AsiA$_{His}$). When the purified ligation product and the corresponding amount of the cleavage product were combined with $E.$ $coli$ RNA polymerase core, the resulting holoenzymes were active on the ga/P1 promoter as was the holoenzyme reconstituted with full-length recombinant $\sigma^{70}$ (FIG. 5B). The ga/P1 promoter belongs to the "extended −10" promoter class, and is active even in the absence of sigma region 4.2 (29). From this experiment, it can be concluded that both the cleavage and the ligation products retained their biological activity during the overnight incubation with 2% thiophenol.

A similar experiment was repeated on the T7 A2 promoter. T7 A2 is a strong promoter of the "−10/−35 class" and requires interaction between σ region 4 and the −35 box for its activity. As can be seen from the autoradiogram shown on FIG. 2C the holoenzyme reconstituted with the ligation product was almost as active as the holoenzyme reconstituted with the full length recombinant $\sigma^{70}$. In contrast, the holoenzyme reconstituted with the cleavage product was completely unable to support transcription by the core enzyme on T7 A2 (lane 3). It was concluded that the semisynthetic, 600 amino acids long $\sigma^{70}$ derivative is functional in promoter-dependent transcription. The results also establish, as expected, that the non-natural cysteine introduced at the ligation site does not interfere with $\sigma^{70}$ function, and, in agreement with the data of Kumar et al. (45) that the last 13 amino acids of $\sigma^{70}$ are not necessary for unregulated transcription.

The results presented in FIG. 5A demonstrate that $\sigma^{70}$ amino acids 567–600 are necessary for AsiA binding. In order to show that $\sigma^{70}$ amino acids 557–600 are also sufficient for interaction with AsiA we performed a Ni$^{2+}$-NTA agarose co-immobilization experiment with the synthetic σ 33-mer. Two different experiments were performed, and the same result was obtained. The first experiment was essentially a repetition of the experiment shown in FIG. 5A, and demonstrated that the synthetic 33-mer can be immobilized on Ni$^{2+}$-NTA agarose through AsiA$_{His}$. The complementary experiment was done using wild type, untagged AsiA. Instead, a synthetic hexahistidine tag was chemically ligated to the N-terminus of σ568-600 as described herein. AsiA and His-tagged σ fragment were loaded on Ni$^{2+}$NTA beads, the beads were washed and eluted with increasing concentrations of imidazole in the buffer. As can be seen, AsiA was found in the fractions containing elevated concentrations of imidazole and the elution profiles of AsiA and His-tagged $\sigma_{568-600}$ from Ni$^{2+}$-NTA agarose beads were identical, indicating strong interaction. A control experiment showed that AsiA did not interact with Ni$^{2+}$-NTA agarose. It was concluded that $\sigma^{70}$ amino acids 568–600 are sufficient for interaction with AsiA.

This preparation, affords a 600 amino acid long semisynthetic $\sigma^{70}$ protein with an intact biological function. This molecule was used to map the determinants of AsiA binding within amino acids 567–600 of $\sigma^{70}$. Results are in excellent agreement with that of Colland et al. who used hydroxyradical protein-protein footprinting to demonstrate that the only region of $\sigma^{70}$ that is protected from radical cleavage by AsiA is located between residues 572 and 588. $\sigma^{70}$ amino acids 567–600 comprise the evolutionary conserved region 4.2 of the σ family of proteins. This region is thought to assume a helix-turn-helix conformation and to interact directly with the −35 box of the promoter. The present results, taken together with the finding that the binding of region 4.2 to the −35 box or AsiA is mutually exclusive, suggests that AsiA may inhibit transcription directly, by occluding the DNA binding surface or region 4.2.

The results presented here illustrate the enormous potential of the expressed protein ligation technique for exploring the mechanism and regulation of complex biomolecular machines. In the case of E. coli RNA polymerase, it was demonstrated that the ligation conditions do not destroy protein function and that semi-synthetic $\sigma^{70}$ subunits can be reconstituted with the RNA polymerase core enzyme to give a fully functional holoenzyme. Thus, the method of the present invention can be utilized to introduce into the $\sigma^{70}$ subunit site-specific biochemical and biophysical probes. For example, introducing cross-linkable probes can be introduced site specifically into semisynthetic $\sigma^{70}$. Promoter complexes formed by RNA polymerase holoenzymes reconstituted with derivatized, cross-linkable sigmas will allow the study of protein-protein and protein-nucleic acids contacts that govern transcription activation and promoter recognition. Other subunits of the E. coli RNA polymerase complex can be reconstituted in vitro, since expressed protein ligation will have widespread utility in this multi-protein system.

In essence, the alkyl thioester substituents of the present invention may be relatively unreactive wherein there is not the presence of a good leaving group. Such a relatively unreactive substituent yield an important advantage in facilitating isolation, purification and storage of the derivative prior to the ligation step. The subsequent addition of an electron withdrawing group to the relatively stable derivative can be used to initiate rapid intramolecular rearrangement and formation of the amide bond in the ligation step. This step is referred to as "ligation ramp up." For example, addition of thiophenol to the stable relatively unreactive derivative will initiate the rapid ligation step as described herein. Other chemicals and compounds capable of adding an electron withdrawing group (and thus achieving "ligation ramp up") to the relatively unreactive alkyl thioester derivatives are well known in the art. The ability to isolate, purify and store the relatively unreactive alkyl thioester derivative facilitates the insertion of a variety of modified and unmodified molecules into a target protein or peptide or analog thereof.

As used herein, "pM" means picomolar, "nM" means nanmolar, "uM" or "$\mu$M, means micromolar, "mM" means millimolar, "ul" or "$\mu$l" mean microliter, "ml" means milliliter, "l" means liter.

As used herein, the term "synthetic amino acid" means an amino acid which is chemically synthesized and is not one of the 20 amino acids naturally occurring in nature. As used herein, the terms "non-natural amino acid" and "unnatural amino acid" means an amino acid which is not one of the 20 amino acids naturally occurring in nature. Thus, a synthetic amino acid is an unnatural amino acid.

As used herein, the term "biosynthetic amino acid" means an amino acid found in nature other than the 20 amino acids commonly described and understood in the art as "natural amino acids." Examples of "non-amide isosteres" include but are not limited to secondary amine, ketone, carbon-carbon, thioether, and ether moieties.

As used herein, the term "non-natural peptide analog" means a variant peptide comprising a synthetic amino acid. As used herein, "NMR" means nuclear magnetic resonance, "ESMS" means electrospray mass spectrometry; "CBD" means chitin binding, domain; "SH2" means src homology type-2 domain; "Abl" means human Abelson protein tyrosine kinase, "GST" means glutathione S-transferase; "HSQC" means heteronuclear single-quantum correlation spectroscopy. "HPLX" means high pressure liquid chromatography; "PhSH" means thiophenol, "BzlSH" means benzyl mercaptan; standard single and triple letter codes for amino acids, and single letter codes for nucleic acids are used throughout.

A "segment" as the term is used herein, consists of a portion of a protein or peptide primary amino acid sequence. Such a segment as used herein may be generated by proteolytic cleavage, chemical cleavage or physical disruption. Alternatively, such a segment may be generated by an expression vector or by an in vitro translation of an RNA transcript or portion thereof. Such a segment may assume a structural conformation or folding pattern which is unique to the segment or which represents the conformation of the segment in the complete protein or peptide.

A "domain" as used herein, is a portion of a protein that has a tertiary structure. The domain may be connected to other domains in the complete protein by short flexible regions of polypeptide. Alternatively, the domain may represent a functional portion of the protein.

As used herein, amino acid residues are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. Abbreviations for amino acid residues are used in keeping with standard polypeptide nomenclature delineated in J. Biol. Chem., 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Amino acids with nonpolar R groups include: Alanine, Valine, Leucine, Isoleucine, Proline, Phenylalanine, Tryptophan and Methionine. Amino acids with uncharged polar R groups include: Glycine, Serine, Threonine, Cysteine, Tyrosine, Asparagine and Glutamine. Amino acids with charged polar R groups (negatively charged at pH 6.0) include: Aspartic acid and Glutamic acid. Basic amino acids (positively charged at pH 6.0) include: Lysine, Arginine and Histidine (at pH 6.0). Amino acids with phenyl groups include: Phenylalanine, Tryptophan and Tyrosine. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free NH$_2$ can be maintained. Amino acids can be in the "D" or "L" configuration. Use of peptidomimetics may involve the incorporation of a non-amino acid residue with non-amide linkages at a given position.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The detectable marker labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The proteins and peptides of the present invention can also be labeled with a radioactive element or with an enzyme. The radioactive label can be detected by any of the currently available counting procedures. The preferred isotope may be selected from $^3$H, $^{13}$C, $^{15}$N, $^{14}$C, $^{32}$P, $^{35}$S, $^{36}$Cl, $^{51}$Cr, $^{57}$Co, $^{58}$CO, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A basic description of nucleic acid amplification or PCR (polymerase chain reaction) is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, E. coli DNA polymerase I, thermostable Taq DNA polymerase, Klenow fragment of E. coli DNA polymerase I, T4 DNA polymerase, other available DNA polymerases, reverse transcriptase and other enzymes which will facilitate combination of the nucleotides in the proper manner to form amplification products. The oligonucleotide primers can be synthesized by automated instruments sold by a variety of manufacturers or can be commercially prepared based upon the nucleic acid sequence of this invention.

As used herein, the term "chip" means any solid support including, but not limited to silicon, glass, polypropylene, polystyrene, cellulose, plastic and paper. Accordingly, the term "protein chip" means a protein covalently bound to a solid support including, but not limited to, silicon, glass, polypropylene, polystyrene, cellulose, plastic and paper. The "protein" component of a protein chip as used herein is the ligation product of an oligopeptide and a recombinantly expressed protein or portion thereof, the peptide being the component covalently bound to the solid support. Additionally, as used herein, the term "antibody chip" means an antibody or the antigen-binding portion thereof covalently bound to a solid support as the ligation product of an oligopeptide and a recombinantly expressed antibody protein or portion thereof, the peptide being the component covalently bound to the solid support. Furthermore, as used herein, the term "antigen chip" means an antigen covalently bound to a solid support as the ligation product of an oligopeptide and a recombinantly expressed antigenic protein or portion thereof, the peptide being the component covalently bound to the solid support. Moreover, the term "protein chip protein" refers to the protein component of the protein chip which is the ligation product produced by the methods disclosed by the present invention.

The following examples are presented in order to more fully illustrate the preferred embodiments of the invention. They should in no way be construed, however, as limiting the broad scope of the invention. While the invention is described and illustrated herein by references to various specific material, procedures and examples, it is understood that the invention is not restricted to the particular material combinations of material, and procedures selected for that purpose. Numerous variations of such details can be implied as will be appreciated by those skilled in the art.

EXAMPLES

Example 1

An intein-CBD expression plasmid containing full-length wild-type human Csk DNA was generated and co-expressed in E. coli along with GroES and GroEL. Primers containing an NdeI site (upstream) and a SmaI site (downstream) were used to PCR amplify full-length wild type human csk DNA for in frame insertion upstream of the intein/chitin binding domain encoding sequence in the vector pCYB2 (NEB). The resultant plasmid pCYB2-CSK which was free of mutations in the Csk coding region based on DNA sequencing was then co-transformed into E. coli DH5α with the GroESL expression plasmid pREP4-groESL using dual selection with ampicillin and kanamycin and cells grown and lysed as described by Grace et al., Biochemistry 36, 1874 (1997). Chitin resin (1 ml) in a disposable plastic column was washed with 20 mL of equilibration buffer (25 mM NaHEPES, pH 7.0, 250 mM NaCl, 1 mM Na-EDTA, 0.1% Triton X-100). Cell lysate (10 mL, made 0.1% in Triton X-100) was passed through the column at a flow rate of 0.5 mL/min and the flow-thru was re-applied at a similar rate. The column was then washed with 30 mL of equilibration buffer and treated with 2 mL 2% v/v thiophenol in equilibration buffer (minus Triton X-100) at 1 mL/min followed immediately by 1 mL of 2 mM peptide+2% thiophenol+ equilibration buffer (minus Triton X-100). After 24 hours standing at 25° C., the column was eluted with equilibration buffer and the desired product appeared in the initial 2.5 mL; it was dialyzed (Dispodialyzer™, 25 kDa cutoff, Fisher Co.) against 25 mM NaHEPES, pH 7.7, 2 mM dithiothreitol, 500 mM NaCl at 4° C. for 4–5 d to remove unligated peptide. Protein was estimated to be approximately 20% pure by SDSPAGE with the principal contaminants presumed to be GroEL (60%) and DnaK (20%) (see FIG. 2B). Quantification of the semi-synthetic Csk proteins was based on the intensity of Coomassie blue stained bands on SDSPAGE compared to known amounts of wild type Csk and relative amounts of Csk semi-synthetic proteins further confirmed by quantitative fluorescence imaging (Storm, Molecular Dynamics).

The soluble fraction was passed over chitin resin and the resin was washed and then treated with 50 mM dithiothreitol containing buffer overnight. This led to generation of full-length Csk protein. Kinase assay of the Csk generated in this manner showed that it was fully active. Treatment of the resin bound Csk-intein-chitin fusion with mercaptoacetic acid and cysteine also afforded comparable quantities of Csk (whereas treatment with N-acetylcysteine, for reasons that are unclear, gave no detectable yield of Csk).

With these results, the tyrosine phosphorylated and unphosphorylated forms of the peptide NH$_2$-Cys-Glu-Asp-Asn-Glu-Tyr-Thr-Ala-Arg-Glu-aminocaproate-Lys-ε-[fluorescein]-CO$_2$H (SEQ ID NO: 2) were designed and synthesized. Phosphorylated and unphosphorylated peptides were manually synthesized by Boc and Fmoc solid phase peptide synthesis, respectively. Phosphotyrosine was introduced during Fmoc chain assembly in the phosphate unprotected form. Orthogonal protection of the —NH$_2$ group of the C-terminal Lys residue with either Fmoc (Boc-strategy) or dde (Fmoc strategy) allowed direct attachment of fluorescein (activated as an Nhs ester) prior to the final cleavage step. Following cleavage, peptides were purified to homogeneity by HPLC and characterized by electrospray mass spectrometry. This sequence is derived from the highly conserved activating autophosphorylation site of Src family kinases (9, 10). In its tyrosine phosphorylated form, a similar sequence has been shown to bind specifically to the SH2 domain of Csk (21–23) The N-terminal cysteine residue was included in the peptide to facilitate native chemical ligation. Incorporation of a carboxy-terminal fluorescent tag via a flexible linker was envisaged to serve as a sensitive marker of successful ligation and as a probe for further biochemical studies.

Figure 2A:
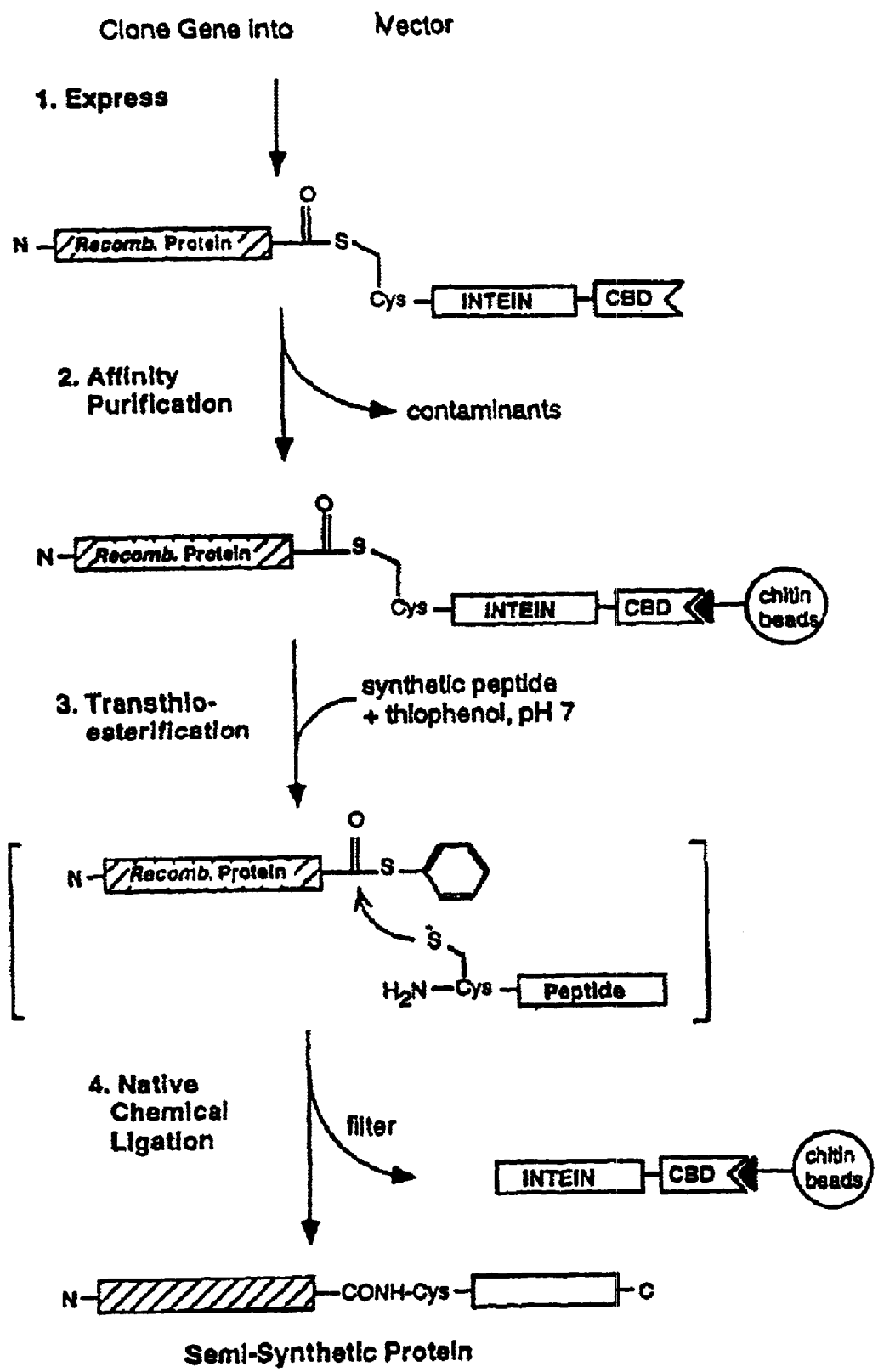
FIGS. 2A–2C. is a reaction scheme showing the synthesis and characterization of semi-synthetic proteins via the method of expressed protein ligation. In the first step, the gene or gene fragment is cloned into the commercially available PCYB2-IMPACT™ vector (New England Biolabs) using the NdeI and SmaI restriction sites. Importantly, this cloning strategy results in the addition of a glycine residue at the C-terminus of the protein of interest, thereby accelerating the rate of the subsequent ligation reaction (22) and reducing the chance of side reactions. Following expression and affinity purification of the fusion protein by binding to the chitin resin, the chemical ligation step is initiated by incubating the resin-bound protein with thiophenol and synthetic peptide in buffer. This results in the in-situ generation of a highly reactive phenyl α-thioester derivative of the protein which then rapidly ligates with the synthetic peptide to afford the desired semi-synthetic protein.
Figure 2B:
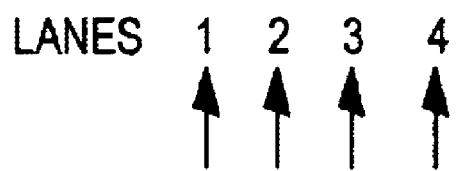
Figure 2B:
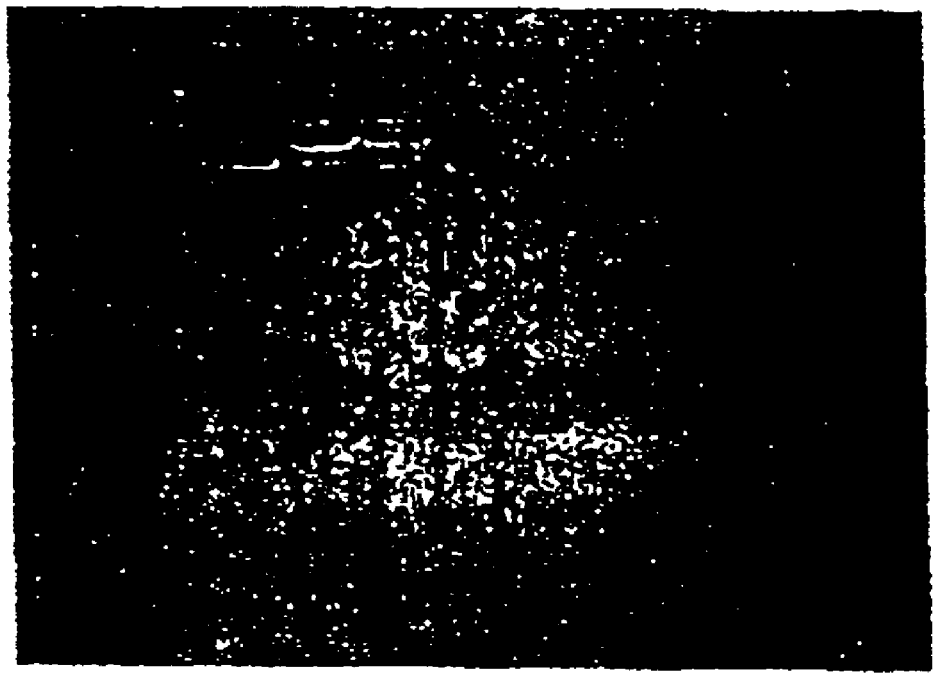
Figure 4:
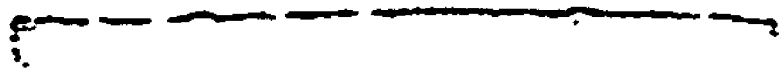
FIG. 4. shows the fluorescence imaging of an SDSPAGE showing the results of proteolytic digestions of $Csk^{PEP}$ and $Csk^{pPEP}$ with subtilisin Lane 1: $Csk^{pPEP}$ minus subtilisin; Lane 2: $Csk^{pPEP}$ plus subtilisin; Lane 3: $Csk^{PEP}$ minus subtilisin; Lane 4: $Csk^{PEP}$ plus subtilisin. Reactions conditions: $Csk^{PEP}$ and $Csk^{pPEP}$ (1 μg) in 20 μL buffer (20 mM Tris-acetate, pH 8.0, 10% glycerol, 2 mM dithiothreitol) treated with subtilisin Carlsberg (12.5 ng) for 30 minutes at 4° C. Fluorescence imaging done on a Storm instrument (Molecular Dynamics).
Figure 4:
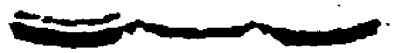
Figure 4:

Initial efforts to react the unphosphorylated peptide with the resin-bound Csk-intein-CBD fusion protein without added thiol cofactors were unsuccessful, and co-addition of mercaptoacetic acid led to cleavage of Csk from the fusion protein, without any detectable ligation. However, inclusion of 2% thiophenol in the reaction buffer led to extremely efficient (greater than 90%) ligation of the synthetic peptide to the recombinant protein as evidenced by the production of a highly fluorescent 52 kDa protein band on SDSPAGE (FIG. 2B, FIG. 4). As illustrated in FIG. 2A, it is hypothesized that a two-step, one-pot process involving an initial transthioesterification event followed by immediate native chemical ligation occurs. The initial transthioesterification step is critical as it alleviates any steric hindrance present around the fusion protein thioester, and creates a reaction sink involving the formation of a highly reactive phenyl α-thioester derivative of the recombinant Csk protein (22). The corresponding mercaptoacetic acid thioester would be expected to be much less reactive than the phenyl thioester thus accounting for the results in preliminary studies.

Figure 2C:
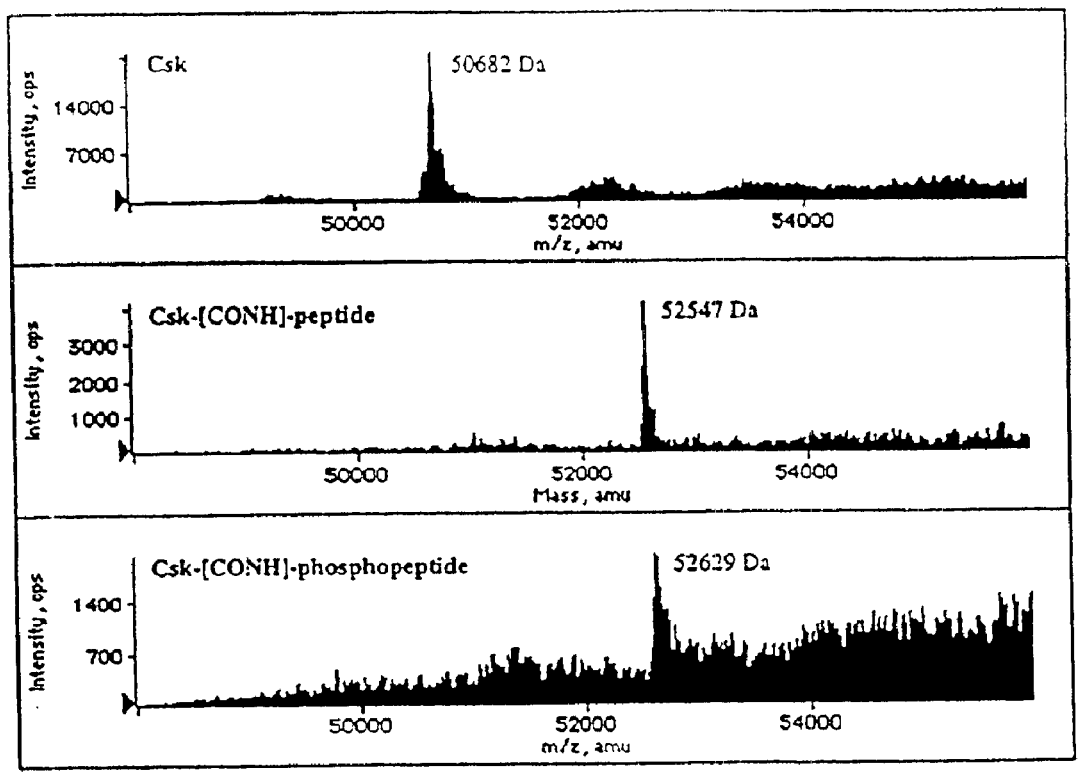

In each of the two ligation reactions, the crude product mixture was nearly free of unligated material, although both preparations were contaminated with GroEL and DnaK. Although yields were not optimized, an estimated 0.5 mg of ligation product per 2.5 L bacterial cell culture was produced. Ligation conditions were not disruptive to Csk protein folding since both Csk-[CONH]-peptide (Csk$^{PEP}$) and Csk-[CONH]-phosphopeptide (Csk$^{pPEP}$) had similar catalytic activity to wild type and nearly identical activity to each other. Kinase assays were performed as described by Cole et al., *J. Biol. Chem.* 269, 30880 (1994) where transfer of $^{32}$P from γ-$^{32}$P-ATP to poly(glu,tyr) was monitored. Briefly, poly(glu,tyr) reactions were carried out in 60 mM Tris-HCl, pH 7.4, 2 mM MnCl$_2$, 10 mM dithiothreitol, 200 μg/mL BSA for 2 minutes at 30° C., quenched with EDTA, run out on 10% SDSPAGE and phosphopoly(glu,tyr) analyzed by scintillation counting. Velocity measurements were based on initial conditions where reaction of the limiting substrate did not exceed 10%. Autophosphorylation of the semi-synthetic Csk ligation proteins was shown to be insignificant. Kinetic parameters were as follows: Csk$^{PEP}$, K$_m$ of ATP=31±2 μM, K$_m$ of poly(glu,tyr)=19±3 μg/mL, k$_{cat}$=17±1 min$^{-1}$; Csk$^{pPEP}$, K$_m$ of ATP=34±11 μM, K$_m$ of poly(glu,tyr)=30±3 μg/mL, k$_{cat}$=19±1 min$^{-1}$; wild type Csk (32), K$_m$ of ATP=12±1 μM, K$_m$ of poly(glu,tyr)=48±2 μg/mL, k$_{cat}$=40±5 min$^{-1}$. Further characterization of (Csk$^{PEP}$) and (Csk$^{pPEP}$) by electrospray mass spectrometry gave molecular masses in good agreement with the predicted values (FIG. 2C). Interestingly, Edman sequencing revealed that the N-terminal methionine residue in the protein produced as an intein-CBD fusion was completely removed (no such cleavage is observed when Csk is expressed in the standard form).

The novel Csk ligation products were subjected to extensive dialysis to remove unreacted peptide. Following dialysis, affinity purification over a phosphotyrosine column (19) was attempted for both Csk$^{PEP}$ and Csk$^{pPEP}$ in order to assess potential conformational differences. While about 50% of Csk$^{PEP}$ bound to the phosphotyrosine resin under low salt conditions, comparable to wild type Csk, only about 10% Csk$^{pPEP}$ bound to the phosphotyrosine resin under similar conditions. It is presumed that the SH2 domain of Csk$^{pPEP}$ is less available for affinity column interaction because it is pre-bound to the phosphotyrosine sequence of Csk$^{pPEP}$. Similar behavior has been reported with Src family members (9, 19).

Figure 3:
FIGS. 3A–3B. shows the non-denaturing PAGE of tail phosphorylated and unphosphorylated forms of a Src family member and Csk. The non-denaturing PAGE was performed using 6% polyacrylamide with 10% v/v of 2-mercaptoethanol in the gel load solution.
Figure 3:
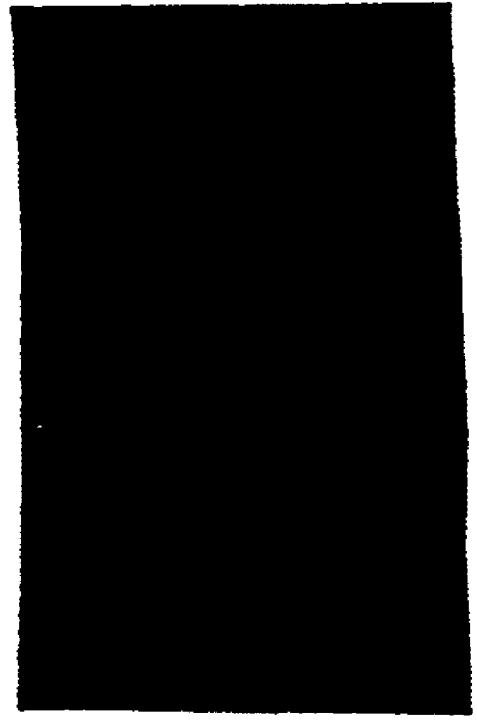

In the case of Src family members, the interaction between the phosphotyrosine tail and the SH2 domain has been shown to be intramolecular (11, 12, 14). Non-denaturing PAGE (6%) with fluorescence imaging showed that Csk$^{pPEP}$ had a slightly faster migration time compared to Csk$^{PEP}$, consistent with Csk$^{pPEP}$ having a slightly smaller Stoke's radius and/or an increased electrostatic effect (FIG. 3A). A non-denaturing PAGE of the Src family member Lck in its tail-phosphorylated and unphosphorylated form showed very similar behavior (FIG. 3B). Gel filtration showed that both the semi-synthetic Csk proteins were monomeric, evidence that the proposed interaction between the phosphotyrosine tail and SH2 domain in Csk$^{pPEP}$ is intramolecular. Gel filtration for both proteins was carried out on a Superdex-75 column (Pharmacia) in 20 mM Tris-acetate, pH 8.0 at 0.5 mL/min at room temperature using the proteins ribonuclease A (13,700 kDa), carbonic anhydrase (29 kDa), ovalbumin (43 kDa), and bovine serum albumin (66 kDa) to generate a standard curve. Detection of the standards and wild type Csk was done by monitoring UV absorbance at 280 nm and for the semi-synthetic Csk proteins was done by monitoring fluorescence emission at 520 nm. The concentration of the semi-synthetic Csk proteins during column loading was approximately 1 μM. The calculated molecular weights were: wild type Csk (50 kDa), Csk$^{PEP}$ (54 kDa), and Csk$^{pPEP}$ (54 kDa) with an estimated standard error ±10%.

Limited proteolysis studies with subtilisin further suggested a conformational difference between Csk$^{PEP}$ and Csk$^{pPEP}$, with Csk$^{pPEP}$ showing a slower proteolytic degradation rate as demonstrated by the persistent fluorescent bands on SDSPAGE in FIG. 4. The ~38 kDa fragment produced in the proteolysis of Csk$^{pPEP}$ clearly contains an intact C-terminus because of its fluorescence, and is approximately 7 kDa larger than the primary site of wild type Csk cleavage under similar conditions, with the cleavage site in the latter at the SH2 domain-catalytic domain junction. The position of cleavage in Csk$^{pPEP}$ is nearer to the N-terminal edge of the SH2 domain. Interestingly, tail-phosphorylated and unphosphorylated forms of Src show distinct proteolytic degradation patterns, comparable to those of the semi-synthetic Csk proteins (9, 23). In the case of Src, the overall proteolysis rate is reduced for the tail-phosphorylated form and the C-terminal tail region is particularly resistant to proteolysis when phosphorylated compared to the unphosphorylated form (23).

In sum, the phosphotyrosine affinity, non-denaturing PAGE, gel filtration, and proteolysis results support the proposition that appending a phosphotyrosine tail to Csk results in a new conformation involving an intramolecular interaction between the SH2 domain and the tail phosphotyrosine. Such a conformational switch could lead to new biological activities in cell signal transduction. Further, these results serve as a template for a full understanding of Src and Csk structure and function. The molecules generated in this study could not have been prepared using any previously described technique and demonstrate the enormous potential of manipulating macromolecular conformation through the integration of chemistry and biotechnology.

Example 2

Experimental Procedures

Cloning, Expression, and Purification of Proteins

The plasmid pCYB2-$\sigma_{500-567}$, which expresses a 65 amino acid fragment of $\sigma$ fusion to intein-CBD from an IPTG-inducible trc promoter was constructed by PCR amplification of the corresponding fragment of rpoD and recloning it in NdeI-SmaI treated plasmid pCYB2 (New England Biolabs). pCYB2-$\sigma_{1-567}$ was constructed similarly. The natural NdeI site at codon 452 of rpoD was removed by site-directed mutagenesis to facilitate the cloning. The protein sequence remained the same due to degeneracy of the genetic code. The plasmids were transformed into the E. coli XL1-blue, cells were grown to mid-log phase in LB medium plus 200 mg ampicillin/ml, and induced with 1 mM IPTG overnight. The expression level was low (>1 mg/l), and we could barely detect the band of the overexpressed proteins on SDS-gels.

After recovery by centrifugation, cells were resuspended in 40 ml of 50 mM Tris-HCl, 500 mM NaCl, 10 mM EDTA, pH 7.9 and lysed by passage through a French press, and the lysate was cleared by low speed-centrifugation. The overexpressed proteins were recovered from the cytosolic fraction by affinity chromatography on a 2 ml chitin column equilibrated in the same buffer as suggested by the manufacturer. The column was washed with 50 ml of buffer, and 25 ml 0.2 M phosphate buffer, pH 7.3, 0.2M NaCl; drained, and the beads were stored as a 50% suspension in the same buffer at 4° C. until further use.

AsiA was purified as described by Severinova et al., (18). Plasmid expressing AsiA genetically fused to a C-terminal promoter was provided by D. Hinton. The protein was overexpressed in BL21 (DE3) cells and purified to homogeneity by IMAC. AsiA proteins were concentrated using a Centricon 3 centrifugal filter (Amicon) and stored at –20° C. in a buffer containing 50% glycerol.

Synthesis of Peptides

All peptides were chemically synthesized according to optimized Boc SPPS (15), and purified by preparative reverse-phase HPLC using a Vydac C-18 column. In all cases, peptide composition and purity was confirmed by electrospray mass spectrometry and analytical HPLC. Fluoroscein was attached to the $\epsilon$-amino group of the lysine residue in the peptide NH$_2$-CEDNEYTARE-aminocaproate-K—CO$_2$H (SEQ ID NO: 3) prior to the final cleavage/deprotection step using a Boc-Lys-$\epsilon$-(NH-Fmoc) orthogonal protection strategy. The construct His$_6$-Cys-[SCH$_2$]-aminocaproate-$\sigma_{568-600}$ was prepared by chemically ligating the purified, unprotected peptides NH$_2$-His$_6$Cys-CO$_2$H and BrAc-aminocaproate-$\sigma_{568-600}$ using the previously described thioether-based chemical ligation strategy (10).

Protein Ligation

100–500 $\mu$l of 50% chitin bead suspension was combined with various co-factors in the presence or in the absence of 1 mM synthetic peptide. Co-factors were used at 100 mM concentration (DTT, mercaptoacetic acid, N-acetyl cysteine, and cysteine), and 2% v/v (thiophenol). Reactions were performed in 0.2 M phosphate buffer, pH 7.3, 200 mM NaCl (DTT, thiophenol, and cysteine), or 0.5 M phosphate buffer, pH 7.3 (N-acetylcysteine and mercaptoacetic acid). All reactions were incubated overnight with gentle agitation and then diluted 10-fold with transcription buffer [20 mM Tris-HCl, pH 7.9, 100 mM KCl, 10 mM MgCl$_2$]. The beads were allowed to settle and the supernatant was dialyzed against two 1 l changes of transcription buffer. The protein was then concentrated on a C-30 concentrator (Amicon, USA) to ~1 mg/ml, diluted two-fold with glycerol and stored at –20° C.

Ni-NTA Binding

100 $\mu$l reactions contained 15 $\mu$l of Ni$^{2+}$-NTA agarose (Qiagen), 50–100 pmol $\sigma^{70}$ or $\sigma^{70}$ derivative, 200 pmol AsiA$_{His}$, 20 mM Tris-HCl, pH 7.9, 100 mM KCl, 10 mM MgCl$_2$. Reactions were preincubated for 15 min at room temperature, after which the beads were pelleted by brief centrifugation and the supernatant, containing the unbound material was removed. The beads were then washed three times with the same buffer containing 10 mM imidazole, pH 8.0, resuspended in 50 $\mu$l of the buffer containing 100 mM imidazole and incubated for additional 15 min at room temperature. The supernatant containing the bound material was then withdrawn. Aliquots of the reactions were then analyzed on 8–25% Phast gels (Pharmacia) and silver stained. For transcription reactions, washed Ni$^{2+}$-NTA agarose beads containing $\sigma^{70}$ or the ligation product immobilized through AsiA$_{His}$ were treated with an equal volume of 7 M guanidine-HCl (15 min at room temperature with agitation). 10 $\mu$l of the supernatants was removed, diluted to 100 $\mu$l with transcription buffer and used for transcription reactions.

In vitro Transcription

Abortive initiation reactions were performed in 20 $\mu$l of transcription buffer containing 20 nM of either the 123-bp T7 A2 promoter containing DNA fragment (17), or 150 bp gal P1 fragment (18), 40 nM RNAP core enzyme, 0.5 mM CpG (T7 A2) or ApU (gal P1) and 50 M $\alpha$-[$^{32}$P]CTP (30 Ci/mmol), 40 mM Tris-HCl (pH 7.9), 40 mM KCl, and 10 mM MgCl$_2$. Reactions were supplemented with 5 $\mu$l (~10 pmoles) of $\sigma^{70}$ or ligation product prepared as described in the previous section. The amount of cleavage product added to the reaction was equal to that of $\sigma^{70}$ or ligation product based on visual inspection of stained SDS-gels. Reactions proceeded for 15 min at 37° C. and were terminated by addition of an equal volume of loading buffer containing 6M urea. Transcription products were analyzed by urea-polyacrylamide gel electrophoresis (7 M urea, 20% polyacrylamide), followed by autoradiography.

Example 3

Chemical Ligation of Folded Recombinant Proteins: Segmental Isotopic Labeling of Domains for NMR Studies This report describes the development of procedures which for the first time allow two folded recombinant protein domains to be efficiently linked together by in vitro chemical ligation reactions. This strategy was used to prepare NMR quantities of the Abelson protein tyrosine kinase regulatory apparatus, Abl-SH(32), in which only one domain was uniformly labeled with $^{15}$N.

Results

The cellular signaling, protein, c-Abl, is one of the few non-receptor protein tyrosine kinases directly linked to human malignancies (64). The kinase activity of c-Abl is tightly controlled in vivo, and is thought to be partly regulated by specific interactions of its Src homology 3 (SH3) and SH2 domains with other cytoplasmic and nuclear proteins (65, 66). The three dimensional structures of the Abl-SH3 and Abl-SH2 domains have been studied in solution by NMR methods both individually (67, 68), and together in the context of the domain pair (68). This level of structural characterization combined with the importance of these regulatory domains in c-Abl function, suggested the Abl-SH(32) domain pair as an excellent target system for segmental labeling studies.

Figure 6:
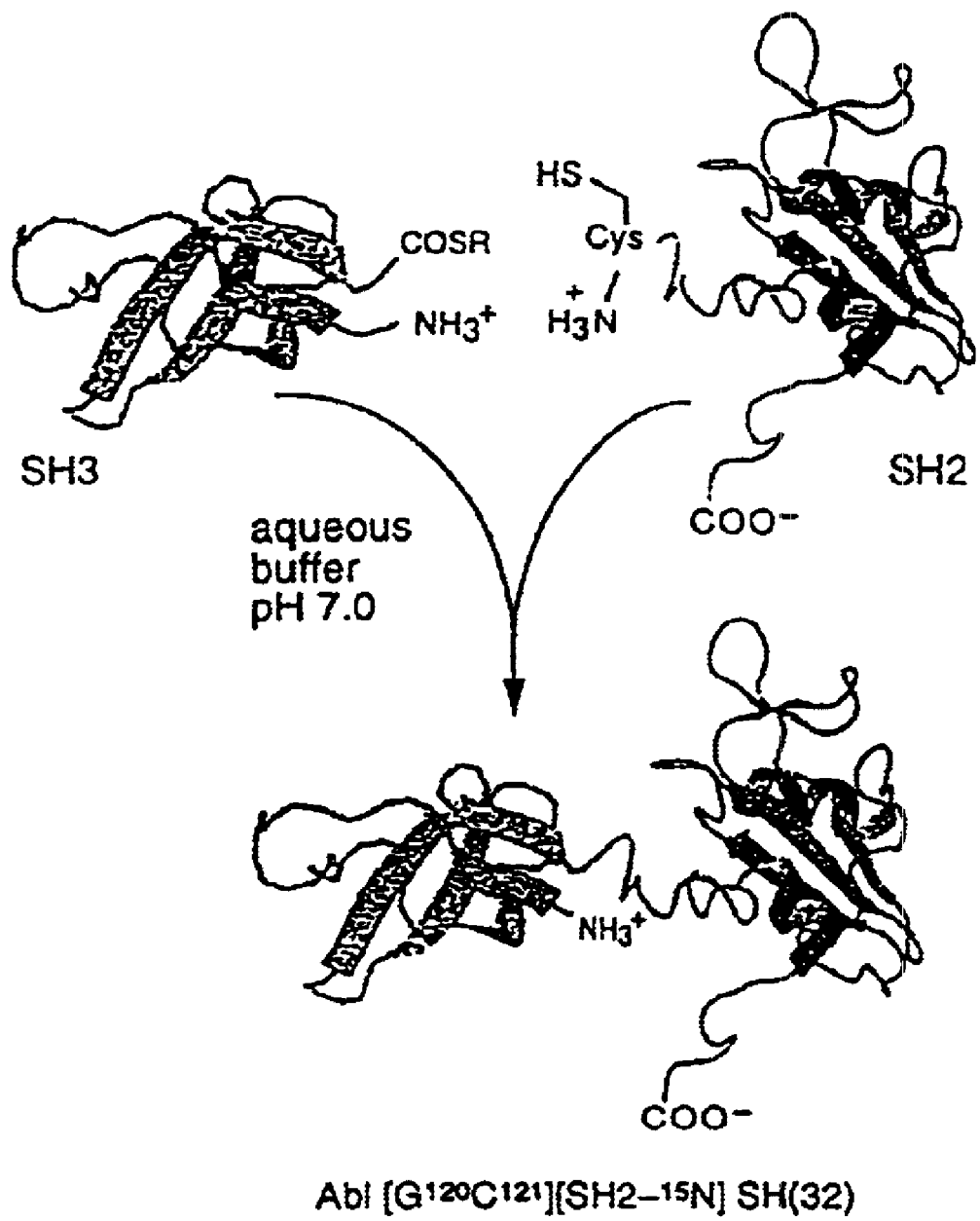
FIG. 6. In vitro chemical ligation of folded recombinant proteins is illustrated by the separation of Abl-SH(32). The Abl-SH3 domain is generated as an $^\alpha$thioester-derivative, and the Abl-SH2 domain is generated with a Cys at the N-terminus. The former is achieved using a modified version of expressed protein fixation (60, 61). Combining the two proteins under conditions which maintain them as folded results in a chemoselective ligation reaction and the generation of a normal peptide bond at the ligation junction (69). The sequence of the final ligation product is m{65}LFVALYDFVAS GDNTLSITKGEKLRVLGYNH-GNGEWAEAQTKNGQGWVPSNYIT-PVGCLEKHSWYHGPVSRNAA EYLLSSGINGSFLVRE-SESSPGQRSISLRYEGRVYHYRINTASDGKLYVSSE SRFNTLAELV HHHSTVADGLITTLHYPAPKR{220} gihrd (SEQ ID NO: 1). Lower case letter indicate non-gene residues from the expression systems used. This construct uses a C$^{101}$S mutation internal to the SH-3 which had previously been inserted to improve stability for NMR experiments. This is also in the 'wildtype' sequence. Native chemical ligation reactions can be performed in the presence of multiple internal cysteine residues in either of the reacting segments (84); only the N-terminal cysteine participates in the ligation reaction.

As Illustrated in FIG. 6, the in vitro chemical ligation strategy called for the generation of a recombinant Abl-SH3 domain activated at its C-terminus as α-thioester, and a recombinant Abl-SH2 domain containing an N-terminal cysteine residue. These two folded protein domains should, when combined under physiological conditions; chemoselectively react via the well established native chemical ligation Reaction (69, 70) to form an amide linkage at the ligation junction. The ligation point was chosen to be located within the short linker region that connects the two domains and involved mutation of the wild-type residues $N^{120}$ and $S^{121}$ to G and C respectively. The Ser-Cys mutation was required to facilitate the ligation reaction, while the Asn-Gly mutation was expected improve the kinetics of ligation. Studies indicate that the majority of natural occurring amino acids (with the exception of Ile, Val and Pro) can be tolerated at the N-terminal side of the ligation junction without dramatically nation yield/kinetics (Hackeng, et al, presented at the Twelfth Symposium of the Protein Society, San Diego, 1998). Thus, in future applications only a single amino acid mutation (i.e. X→Cys)]I may be necessary for expressed protein ligations. Residue numbering is referenced to the complete Abl protein; the $C^{121}$ mutation is then the N-terminus of the Abl-SH2 domain. Previous studies indicated this linker region to be relatively flexible (68) and it was anticipated that the mutations would lead to minimal significant structural perturbations.

It has been shown that intein-CBD fusion proteins can be used as a source of recombinant protein thioesters for chemical ligation reactions (60, 70). The Abl-SH3 sequence (residues Leu$^{65}$ to Val$^{119}$) was subcloned into the commercially available pCYB2 expression vector which allowed the generation of an Abl-SH3-inteinCBD fusion protein. Following, soluble expression in E. coli, the desired fusion protein was affinity purified on chitin beads. A small aliquot of the loaded beads was treated overnight with DTT and the reaction supernatant was analyzed by reverse-phase HPLC and electrospray mass spectrometry (ESMS). This indicated that the expected Abl-SH3 construct was present in >90% homogeneity and that approximately 0.35 ma of the Abl-SH3 domain was immobilized per ml of chitin beads.

Initial attempts to generate the [$C^{121}$]SH2 construct involved cyanogen bromide cleavage of a GST-Abl-SH(32) fusion containing a unique Met-Cys unit at the appropriate position within the intein-domain linker. The Met-Cys unit was introduced into the linker region connecting the Abl-SH3 Zinc Abl-SH2 domains by cassette mutagenenesis using, a NcoI and XmaI restriction strategy. This resulted in Asn 120-→Met and Ser 121 Cys mutations in the Abl-SH (32) construct. The Abl-SH(32) sequence does not contain any endogenous Met residues. This synthetic strategy was unsuccessful because of irreversible oxidation of the cysteine residue to cysteic acid during the chemical cleavage step; the resulting CYS($O_3$H)-Abl-SH2 analog could not participate in subsequent chemical ligation reactions. An alternative approach was therefore employed which utilized the Factor Xa cleavage strategy previously described by Verdine and co-workers (71). In this approach a GST-Abl-SH(32) fusion protein was generated which contained an -Ile-Glu-Gly-Arg-Cys- (SEQ ID NO: 9) motif within the linker region connecting the Abl-SH3 and Abl-SH2 domains. Proteolysis of this fusion protein with Factor Xa afforded the desired [$C^{121}$]SH2 construct in good yield. A similar strategy was also used to prepare uniformly $^{15}$N labeled [$C^{121}$]SH2 (see Materials and Methods).

Preliminary ligation studies investigated whether a short synthetic peptide, $NH_2$-CGRGRGRK[fluorescein]-$CONH_2$ (SEQ ID NO: 4) could be reacted with the immobilized Abl-SH3-intein-CBD fusion protein. Consistent with previously published examples (60, 61) nearly quantitative ligation of the synthetic peptide to the recombinant Abl-SH-3 domain was observed, as indicated by reverse-phase HPLC, ESMS and fluorescence spectroscopy. These studies thus established that expressed protein ligation reactions could be performed on the folded Abl-SH3 domain.

Initial attempts to ligate [$C^{121}$]SH2 to the immobilized SH3/thioester domain led to no detectable product formation. These studies used approximately equimolar amounts of the two reactants, requiring ~2 ml of beads for every milligram of [$C^{121}$]SH2 used. The net effect of performing this reaction directly from the chitin beads was therefore to greatly dilute the [$C^{121}$]SH2 domain (<50 μM), leading to a kinetically unfavorable reaction. It is well established that for efficient chemical ligation reactions, high concentrations (near nM) of both reactants are required (69, 70, 72–75). This kinetic problem was not encountered for the model ligation described above, since the synthetic peptide was present in large molar excess and nM concentration. However, emulating these pseudo-first order conditions for the [$C^{121}$]SH2 ligation was impractical due to the large amounts of the protein required (e.g. ~100 mg of ]$C^{121}$]SH2 would be required for a preparative scale 10 ml reaction).

An alternative and more efficient synthetic approach was developed which overcame the kinetic problems associated with using the immobilized Abl-SH3-intein-CBD fusion protein. This generates a soluble, stable a thioester derivative of Abl-SH3 which can be easily purified and stored, but whose reactivity can be modulated through transthioesterification during the ligation reaction. Previous studies have shown that alkyl αthioester derivatives of synthetic peptides are relatively unreactive as acyl donors (30, 31). Overnight exposure of the chitin beads to ethanethiol at pH 6.0 led to the generation of an ethyl α-thioester derivative of the Abl-SH3 domain. This transthioesterification/cleavage reaction was found to be remarkably clean as indicated by HPLC/ESMS analysis of the reaction supernatant and SDS-PAGE analysis of the residual immobilized protein on the chitin beads. The Abl-SH3 ethyl α-thioester derivative was easily purified by HPLC (gel filtration or dialysis could also be used provided the pH is kept at 6.0 or below) and could be stored as a lyophilized powder for several months.

Figure 7:
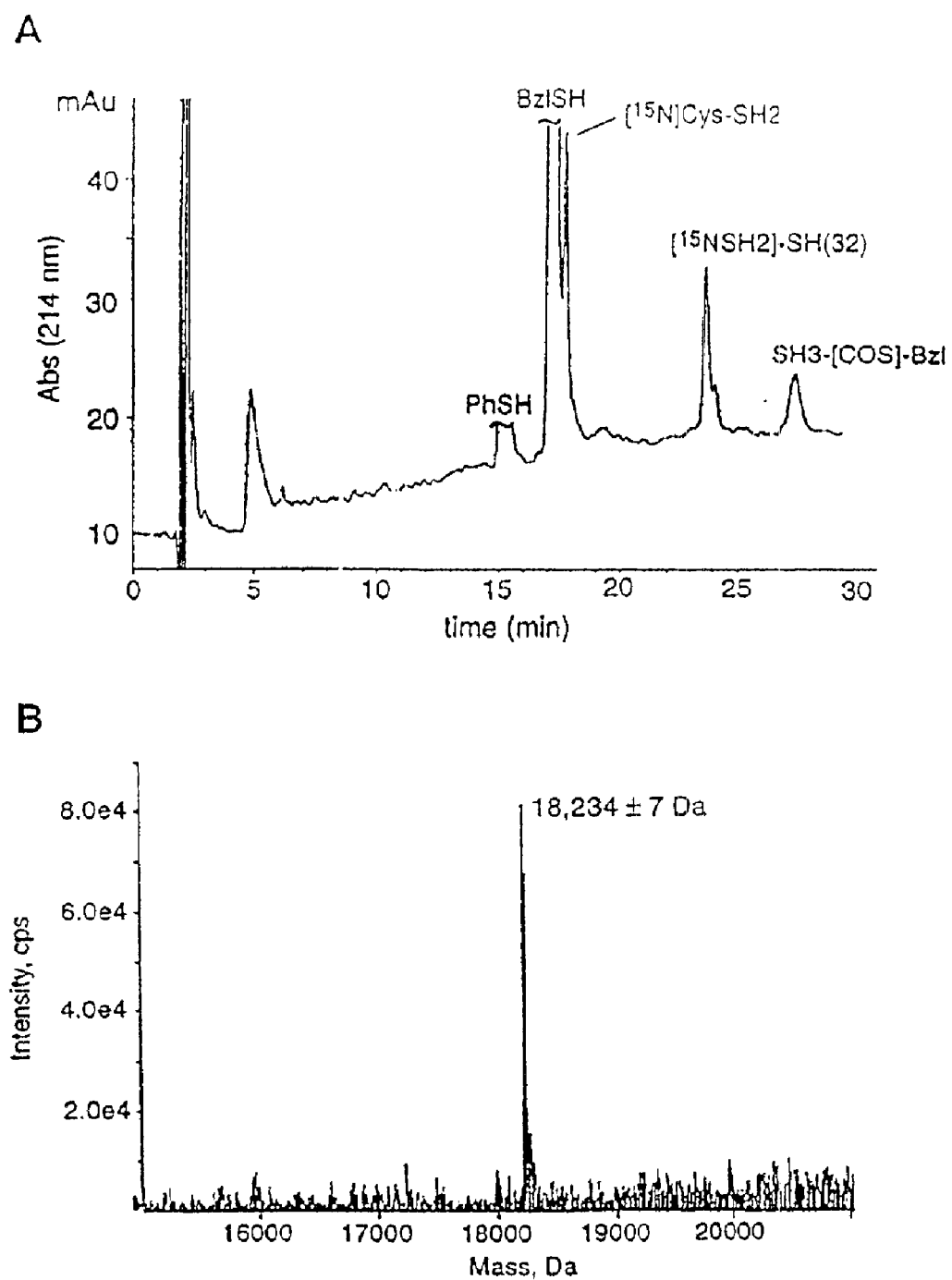
FIGS. 7A–7B. Chemical ligation of Abl[G$^{120}$]SH3 to Abl[C$^{121}$][U-$^{15}$N]SH2.

The [$G^{120}$]SH3 ethyl α-thioester derivative and [$C^{121}$] [$U^{15}$N]SH2 domain were combined in phosphate buffer at pH 7.2, conditions under which the two protein domains are known to adopt stable tertiary folds (67, 68). This appears to be the first time that the chemical ligation of two folded proteins has been attempted. Although chemical denaturants were not present in the example here, such agents can bible, is required, and do not interfere with native ligation chemistry (69, 70, 72–75, 77). Three steps were thus taken to ensure efficient reaction, namely: the two domains were kept at moderately high concentration (~0.5 mM); one of the reactants [$C^{201}$]SH2 was added in molar excess; and the co-factors thiophenol and benzyl mercaptan, were each included in the reaction medium (these are known to catalyze native chemical ligation reactions through in situ transthioesterification (71)). The process of the ligation reaction was monitored using a combination of analytical HPLC and ESMS which indicated the reaction had gone to ~70% completion after 4 days (FIG. 7A). At this point the ligation product, Abl-[$G^{120}0C^{121}$]SH2-15N]SH(32), was purified by preparative HPLC and its covalent structure characterized by ESMS (FIG. 7B).

Preliminary studies had indicated that HPLC purified recombinant Abl-SH(32) could be lyophilized and then refolded by rapid dilution from a 6 M GLIHCI containing buffer into phosphate buffer at pH 7.2. Under these conditions, no protein precipitation was observed and NMR analysis indicated the sample had adopted a native fold. A similar strategy was therefore used to prepare the complete [SH2-$^{15}$N]SH(32) construct for functional and structural analysis. The binding affinity of Abl-[SH2$^{15}$N]SH(32) for the consolidated ligand, $NH_2$-PVpYENV$G_6$> (PPAYPPPPVP$K_{CONH2}$) (SEQ ID NOs: 5 and 6, respectively), which binds both the SH3 and the SH2 domains simultaneously (78) was studied using a fluorescence-based titration assay. (The C-terminal glycyl residue is linked to the N.sub. .epsilon. of lysyl in the second peptide segment). This revealed the equilibration dissociation constant (Kd) for binding to the ligand, 300 nM, was essentially that previously reported for the Abl-SH(32) construct, 249 nm (78). This affinity is characteristic of the dual domain construct.

Figure 8:
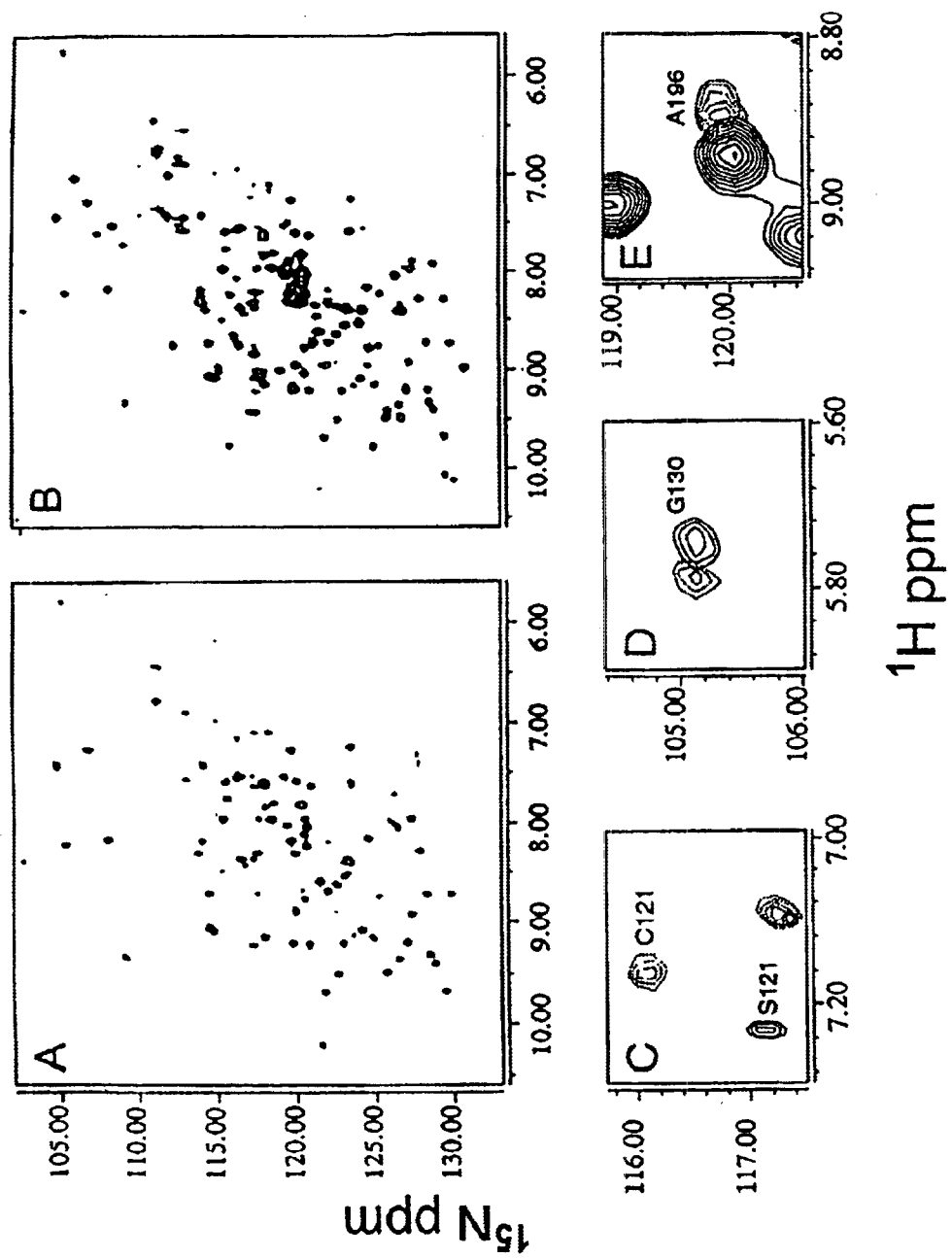
FIG. 8A–8E. 500 MHz $^1$H{$^{15}$N} NMR spectra of FIG. 8A. Abl-[G$^{120}$C$^{121}$][SH2-$^{15}$N]SH(32) and FIG. 8B wildtype Abl SH(32) with uniform $^{15}$N labeling. The peaks in (A) are the SH2-associated subset of those in (B). The peaks showing detectable chemical shift changes away from their position n the wildtype are illustrated in FIGS. 8C–8E.

The purified ligation product was stable under NMR sample conditions. In FIG. 8A, the $^1$H{$^{15}$N}HSQC map of the [$G^{120}C^{121}$][SH2-$^{15}$N]SH(32) may be compared to the [U-$^{15}$N]SH(32); these spectra are essentially fingerprints of the folded proteins. All the peaks of the HSQC map of [G $^{120}C^{121}$][SH2-$^{15}$N]SH(32) almost exactly coincide with those of [U-$^{15}$N]SH(32), and are in agreement with the previous assignments by analogy (68) and from triple resonance data (Xu, R.). There are no extraneous peaks. This NMR data is highly indicative that the structures are very, similar and that the ligation reaction did not affect folding. At the ligation site, chemical shift changes are expected and observed for the NS→GC double mutation, and the $^{15}$N-labeled amide of $C^{121}$, assigned by analogy and difference, indicates the expected standard amide bond formation after the ligation reaction. The $G^{120}$ is not labeled. The new spectra permit identification of the amide for $E^{123}$, previously only ambiguously identified because of low intensity, and overlap with an SH3 amide resonance. Some subtle, but experimentally significant shifts are observed for $G^{130}$ and $A^{196}$ (FIGS. 8D, E). From the expected contacts (67, 68), and observed flexibility of the linker (68, 79), these two residues are believed to be spatially close to the ligation site, where minor effects of the V→G and S→C mutations might be expected for changes in the side chain environment. The small magnitude of these chemical shift perturbations (<0.06 ppm. 'H–, <0.1 ppm $^{15}$N, excluding $S^{121}$C mutation) further support the conclusions that the [$G^{120}C^{121}$][SH2-$^{15}$N]SH (32) is topologically very similar to the wild type.

Conclusions

New approaches to NMR structure determination (54, 80) potentially permit studies of significantly larger systems than those current. The approach of segment labeling, makes assignment and high resolution structural determination practical in systems of high molecular weight, without symmetry. For example, it appears practical to obtain highly resolved fragment spectra for about 100 residues of an 800 residue protein (MW~110 KDa), comparable to those reported for the highly symmetric 7,8 dihydroneoptrin-aldolase, a homo-octomer (50). The effects of 'context' of the surrounding domains on a segmentally labeled domain can now be practically studied by appropriate mutation and chemical ligation. Fragment labeling also permits segmental determination of dynamic properties, residual dipolar couplings (54), and SAR-by-NMR (10). Unlike the previously described trans-splicing approach (59), the chemical ligation strategy presented here can be extended to allow three recombinant protein segments to be regioselectively linked together; the feasibility of such an approach was recently demonstrated in a model synthetic peptide system (75). In principle, this important extension would allow internal domains of a protein to be isotopically labeled for NMR analysis. Other structural uses of this approach might include the incorporation of seleno-methionyl labeled sub-domains into a larger protein, not otherwise available, for use in multi-wavelength anomalous dispersion X-ray experiments for phasing (81), and the incorporation of highly magnetically anisotropic domains to provide additional orientation for NMR dipolar coupling measurements (82).

Materials and Methods

Cloning and Expression of Abl [$C^{121}$]SH2: Suitable SH2 constructs were generated from a pGEX2T vector containing the human Abl-SH(32) coding sequence (20). Two restriction sites, Nco I and XmaI, were introduced either side of the linker region between SH3 to the SH2 domains using polymerase chain reaction (PCR) mutagenenesis. After, treatment with Nco I and Xma I and alkaline phosphatase, a double-stranded 5' phosphorylated DNA cassette (comprising synthetic oligonucleotides 5'-CCG GTC ATC GAA GGT CGT TGC CTG GAG AAA CAT TCC TGG TAT-3' (SEQ ID NO: 7) and 5'-C ATG ATA CCA GGA ATG TTT CTC CAG GCA ACG ACC TTC GAT GA-3' (SEQ ID NO: 8)) was inserted into the pGEX2T plasmid, This oligonucleotide creates an insertion of a Factor Xa cleavage site and a Ser$^{121}$Cys point mutation in the coding sequence. DNA sequencing, was used to confirm the presence of the insertion and mutation. The GST-Abl-SH2-TEGRC-SH2 fusion protein was expressed in *E. coli* DH5-α cells grown in M9 medium using ammonium chloride. Mid-log phase cells were induced with 1 mM isopropyl-1-thio-B-galactopyranoside (IPTG) for 4 hours at 37° C. and harvested by centrifugation. Cells were resuspended in 4.3 mM sodium phosphate, 137 mM NaCl, 2.7 mM KCl, 1.4 mM potassium phosphate, pH 7.2, containing 100 mM EDTA, 1 mM DTT, 1 mM PMSF, 1% v/v Triton-X and 1% w/v aprotinin and then lysed using sonication. The soluble fraction was then passed over glutathione agarose beads which were then washed with 137 mM NaCl, 8 mM sodium phosphate, 2.7 mM KCl, 1.4 mM potassium phosphate, pH 7.2. containing, 100 mM EDTA. Ab3-SH3)-IEGRC-SH2 was cleaved from the glutathione beads using thrombin (23). After thrombin cleavage, Abl-SH3-IEGRC-SH2 was exchanged to Factor Xa reaction buffer (1 mM CaCl, 100 mM NaCl and 50 mM Tris-HCl, pH 7.8, with 0.01% NaN.sub.3). About 200 units of Factor Xa (Pharmacia) were used to cleave 15 mg, Abl-SH3-IEGRC-SH2 in 4 ml reaction buffer at room temperature for 20 hours. The resulting Abl [$C^{121}$]SH2 was Purified by FPLC using a Superdex-75 filtration column (Pharmacia) with 137 mM NaCl, 4.3 mM sodium phosphate, 2.7 mM KCl, 1.4 mM potassium phosphate, pH 7.2, with 2 mM EDTA and 0.1 mM sodium azide as the eluent. The purified protein was concentrated to 0.5 mM using a Centricon concentrator. Purity and characterization was confirmed by analytical HPLC and electrospray mass spectrometry: observed=11,997.8±1.4 Da, expected average isotope comp.)=11,998.2 Da Cloning and Expression of Abl-SH3-Intein-CBD: The gene for the Abl-SH3 domain (residues L65 to V119) was isolated by PCR from a cloned Abl-SH(32) gene (PGEX2T, (20)) using the oligonuceotide primers Abl#1 (5'-GGA TCC CCT GGT CAT ATG CTT TTT GTG GCA CTC TAT GAT TTT GTG-3') (SEQ. ID. NO.: 10) and Abl#2 (5'-ATG TTT CTC CAG GCT GTT AAC GGG GGT GAT GTA GTT GCT TGG-3') (SEQ. ID. NO.: 11). The PCR amplified SH3 domain was purified and digested simultaneously with Nde 1 and Hpa I and then recloned into the NdeI-SmaI treated plasmid pTYB2 (New England Biolabs). The resulting plasmid, pTYB2Abl-SH3, expresses the Abl-SH3 domain fused via a single glycine residue to the intein CBD from an IPTG inducible T7 promoter. The pTYB2Abl-SH3 plasmid was shown to be free of mutations in the Abl-SH3 coding region by DNA sequencing. *E. coli* BL21 cells transformed with pTYB2Abl-SH3 were grown to mid-log phase in Luria Bertani (LB) medium and induced with 1 mM IPTG at 37° C. for five hours. No protein was detected by SDS-PAGE in the soluble fraction of the cell lysate under these conditions. Expression conditions were modified by inducing mid-log phase cells with 0.1 mM IPTG at room temperature for two hours to yield protein in the soluble fraction. After centrifugation, cells were re-suspended in 60 ml of lysis buffer (25 mM HEPES, pH 8.0, 0.1 mM EDTA, 250 mM NaCl, 5% glycerol, 1.0 mM PMSF) and lysed using a French press. The lysate was clarified first by low speed centrifugation and further clarified by ultracentrifugation. The clarified lysate (~45 ml) was loaded onto a 15 ml chitin column pre-equilibrated in column buffer (20 inN HEPES, pH 7.0, 250 mM NaCl, 1 mM EDTA, 0.1% Triton X-100) the column was extensively washed using the same buffer and then stored at 4° C. until further use. The column loading was determined by treating 100 .mu.1 of beads overnight with a buffer containing 0.2 M phosphate, pH 7.2, 0.2 M NaCl, 100 mM dithiothreitol (DTT). Following extensive washing of the beads with 1:1 acetonitrile:water, the amount of cleaved Abl-SH3 in Solution was quantified by analytical HPLC through comparison to an Abl-SH3 standard of known concentration. This analysis indicated a loading of ~0.35 mg/ml of [$G^{120}$]Abl-SH3. Electrospray MS of the cleavage product: observed 6,259.4±0.5 Da, expected (average isotope COMP.)=6,260.0 Da.

Peptide Synthesis: A model peptide $NH_2$-CGRGRGRK[fluorescein]-$CONH_2$ (SEQ. ID. NO.: 4) was chemically synthesized on an MBHA resin using in situ neutralization/HBTU activation protocols for t-butyloxycarbonyl (Boc) solid phase peptide synthesis (38). Orthogonal protection of the E-amino group of the C-terminal Lys residue with fluorenylmethoxycarbonyl allowed solid-phase attachment of fluorescein (activated as it succinimide ester) prior to the final cleavage step. The peptide was purified by reverse phase HPLC and characterized by electrospray MS: observed mass=1,245.9 0.5 Da, expected (average isotope comp.)=1,246.5 Da Model Ligation Reactions: Typically 100 μl of chitin beads were equilibrated with a buffer containing 0.2 M phosphate, 0.2 M NaCl at pH 7.2. To these beads was added a solution of synthetic peptide (1 mg/ml) in the above buffer (100 μl) along with 1.5% v/v thiophenol. The suspension was then gently agitated at room temperature overnight, the supernatant was removed and the beads washed with a 1:1 acetonitrile:water. The combined supernatant and washes were then analyzed by analytical HPLC and electrospray MS indicating the presence of the ligation product in excellent (>90%) yield: observed mass=7,488.0 1.5 Da, expected (average isotope comp.)=7,488.5 Da.

Preparation of Abl[$G^{120}$]-SH3-Ethyl$^\alpha$-thioester: The chitin column, loaded and washed as described above, was equilibrated and suspended in 0.2 M phosphate, pH 6.0, 0.2 M NaCl buffer to which ethanethiol 3% v/v was then added. This suspension was agitated overnight, the supernatant was removed and the beads washed several times with 1:1 acetonitrile:water. All washes were combined with the Supernatant and purified by preparative reverse-phase HPLC using a Vydac C-18 Column. The purity and composition of the resulting Abl-[$G^{120}$]SH3-ethyl$^\alpha$thioester were confirmed by analytical HPLC and electrospray MS: observed mass=6,305.4±1.5 Da, expected (average isotope comp.)=6,304.2 Da.

Preparation of Abl-[$G^{120}C^{121}$][SH2-$^{15}$N]-SH(32): Purified Abl-[$G^{120}$]SH3-ethyl$^\alpha$thioester(2 mg) and Purified $^{15}$N labeled Abl[$C^{121}$]-SH2 (8 mg) were reacted in 1.5 ml of 0.2 M phosphate, pH 7.2, 0.2 M NaCl buffer containing both thiophenol and benzyl mercaptan each at final concentrations of 1.5% v/v. After ~90 hours reaction the desired ligation product was purified by preparative HPLC and characterized by electrospray mass spectrometry; observed mass=18,240.1±5.4 Da, expected (av. isotope comp.)=18,240.2 Da. (see FIG. 7B). The lyophilized heated product (~2.5 mg,) was then dissolved in 200 μl 6M $G_u$HCl, 0.2 M phosphate, pH 7.2, 0.2 M NaCl buffer and refolded by rapid dilution (10 fold) into 0.2 M phosphate, pH 7.2 0.2 M NaCl buffer. The SH3 domain was also prepared with $^{15}$N labeling, observed mass, 6,376.8±0.5 Da. expected (av. isotope composition), 6,378.0 Da. This material could be ligated to [$C^{121}$]SH2)-, resulting analytical quantities of [$G^{120}C^{121}$][SH3-15N]SH(32); observed mass 18,163.3±6.0 Da, expected (av. isotope comp.) 18,156.2 Da.

NMR Measurements on Abl-[SH2-$^{15}$N]SH(32): Protein samples were exchanged into 200 mM NaCl, 4.3 mM sodium phosphate, 2.7 mM KCl, 1.4 mM potassium phosphate, pH 7.2, containing 8% v/v $D_2O$, 2 mM EDTA-$D_{12}$, 0.02% w/v $NaN_3$ in either 2 mM or 10 mM DTT-$D_{10}$ for wild type [U-$^{15}$N]SH(32) and [SH2-$^{15}$N]SH(32) respectively. The final concentration of the heated sample was 0.2 mM and that of the wild type sample 0.8 nM. $^1$H-$^{15}$N HSQC was performed at 35° C. on a DMX-500 NMR spectrometer (Bruker) with a 5 mm probe (Nalorac). The spectral widths were 14 ppm for the $^1$H axis and 33 ppm for the $^{15}$N axis. The spectra were processed using XWINNMR (Bruker). The resulting resolution in the final spectra was 1.75 Hz in the proton dimension, and 3.2-Hz in the $^{15}$N dimension.

Fluorescence Binding Assay: The equilibrium dissociation constants of the protein constructs for the consolidated ligand were determined using the previously described fluorescence-based titration assay (78). The binding constant for the segment labeled construct was 300 (±100) nM. Experiments were performed on a Spex Fluorolog-3 spectrophotometer fitted with a Neslab temperature control unit.

Example 4

The plasmid pCYB2-CSK is used to produce semisynthetic, recombinant CSK protein as described in Example 1. Other intein-expression vectors may be substituted for the pCYB2 vector. Quantification of the semi-synthetic Csk proteins is based on the intensity of Coomassie blue stained bands on SDS PAGE compared to known amounts of wild type Csk and relative amounts of Csk semi-synthetic proteins is further confirmed by quantitative fluorescence imaging (Storm, Molecular Dynamics).

The tyrosine phosphorylated and unphosphorylated forms of the peptide $NH_2$-Cys-Z-Glu-Asp-Asn-Glu-Tyr-Thr-Ala-Arg-Glu-aminocaproate-Lys-ε-[fluorescein]-$CO_2$H (SEQ ID NO: 2) is then designed and synthesized as described above in Example 1. This sequence is derived from the highly conserved activating autophosphorylation site of Src family kinases (9, 10). In its tyrosine phosphorylated form, a similar sequence has been shown to bind specifically to the SH2 domain of Csk (21–23). The N-terminal cysteine residue is included in the peptide to facilitate native chemical ligation. Incorporation of a carboxy-terminal fluorescent tag via a flexible linker serves as a sensitive marker of successful ligation and as a probe for further biochemical studies, including diagnostic screening as described in Example 5 below.

Using a nitrocellulose paper having available amine groups as a solid support, the peptide is covalently bound to the support at the amine groups. While nitrocellulose is used in this experiment, other solid supports are also usable. For example, the solid support may be comprised of silicon, glass, polypropylene, polystyrene, cellulose, plastic or paper. The available amine groups on the nitrocellulose are arranged in an column and row array, providing a grid suitable for high throughput screening. Thus, upon covalent linkage of the peptide to the support, a peptide array is produced. This peptide array is then available for the ligation reaction with the recombinant protein described above and detailed in Example 1.

The protein-peptide ligation reaction is carried out as described in Examples 1 and 2. Thiophenol is included in the reaction buffer in order to promote efficient (greater than 90%) ligation of the synthetic peptide to the recombinant protein.

The novel Csk ligation products bound to the solid support are subjected to extensive dialysis and washing in situ in order to purify the ligated protein product and remove unreacted protein.

The final product is a protein chip composition. Essentially, the nitrocellulose serves as the solid support (chip) which is covalently linked to the peptide which is ligated to the recombinant protein in an grid-like arranged array on the nitrocellulose. The pattern is akin to the pile on a carpet, lined up and available for further interactions, either with protein-binding proteins which will bind the recombinant protein or with antibodies which can recognized the recombinant protein as described in Example 5.

The tag provides a convenient means for identifying a positive interaction.

Discussion

The present invention further contemplates that an antibody or an antigen binding region of an antibody may be covalently bound to a peptide on the chip in order to screen for a specific protein or antigen. Thus, in addition to the protein chip described herein above, an Aantibody chip and an Aantigen chip@ is also contemplated by the present invention.

Furthermore, a Aprotein chip@ suitable for screening in order to identify therapeutic agents is also contemplated by the present invention.

An antibody chip may be used as a diagnostic for the presence of specific proteins or specific protein levels. In particular, an antibody chip is used order to obtain diagnostic information in a clinical setting indicating the presence and amount of pathogens or their products in a sample from a subject. In addition, an antibody chip is used as a research reagent in order to measure changes in proteins or protein levels. In one example, recombinant antibodies are prepared by immunizing mice with an immunogen such as human proteins or pathogens. Reverse transcription-polymerase chain reaction (RT-PCR) of the immunoglobulin hypervariable region using spleen RNA and followed by cloning into phage display vector is performed. Recombinant phage that bind to the immunogen are isolated and plaque purified. The immunoglobulin hypervariable regions are recloned into Heavy and Light Chain Expression Plasmids encoding intein at the C-terminus. Antibodies exhibiting high affinity are identified by testing different combinations of light and heavy chain antibodies. At least two distinct antibodies directed against different epitopes/antigens are recovered. A coupling reagent is introduced at the carboxy terminus of the first antibody using intein chemistry as described above. A flourescent tag is fused to the carboxy-terminus of the antibody directed against the second epitope in order to facilitate rapid identification. Antibodies with the coupling reagent are spotted on chips using a microdispensing robot.

A sample from the subject (i.e. human plasma) is mixed with the antibody chip. Then the flourescent antibodies are applied to the mixture and following washing, detection is measured by fluorescence.

An antigen chip may be used to identify the presence of specific antibodies in a sample from a subject. Recombinant antigens are expressed in an expression vector as described above with Intein at the carboxy terminus. The intein is replaced by a coupling agent and the antigen is spotted on a chip as described above. A sample from a subject is added to the antigen chip under conditions known in the art to be permissive to the formation of a complex. Fluorescent immunoglobulin antibodies are added to the mixture and fluorescent complex formation indicates the presence of antigen in the sample.

A protein chip may be used in order to identify protein-protein interactions and is the basis for a small molecule screen. In this application of the present invention, a protein known to bind other proteins is selected and cloned into an intein vector as described. Novel protein partners are selected using the two hybrid screen or using other methods known in the art. One protein is spotted on a chip via a coupling agent as described above. The second protein (the Abinding partner@) is labeled with fluorescein as described above. Binding complex formation is measured by the presence of fluorescent signal. Small molecule pools (i.e. combinational libraries—biologicals) are added to the chip. Interference with binding is measured by change in fluorescence.

Example 5

Infectious diseases are commonly accompanied by a well-developed humoral immune response. Patients with certain infections often contain large numbers of specific antibody producing cells. One important application of the present invention is a diagnostic screen indicating the exposure of a patient to a given antigen. Such diagnostics can identify development of an immune response which is part of transplantation rejection or metastatic or nascent cancer. Conversely another important application of the present invention is a diagnostic screen indicating the presence of particular antigens, toxins or proteins which are indicative of an ongoing infection or its aftermath.

A protein chip composition produced as described in Example 1 may be used as part of a diagnostic kit in order (a) to identify the presence of a protein in a sample capable of specifically binding the recombinant protein covalently bound to the solid support; (b) to identify the presence of antibody in a sample capable of binding the recombinant protein covalently bound to the solid support; and (c) to identify the presence of an antigen in a sample capable of binding to a recombinant antibody antigen binding region bound to the solid support.

In order to identify proteins in the sample capable of interacting with the recombinant protein bound to the solid support, the sample from a subject is incubated with the protein chip described in Example 4 in a buffered solution at neutral pH for a period of 5 minutes to overnight. Conditions permissive to the formation of protein-protein binding are well known in the art. The protein chip is then extensively washed in buffered solution under non-reducing conditions in order to remove proteins which are not specifically bound to the chip.

Bound proteins are then removed from the solid support for further identification (i.e. SDS-PAGE) although they can also be analyzed in situ. Conditions for removal of the bound proteins are well known in the art and include but are not limited to incubation in buffer under reducing conditions.

In order to identify the presence of antibodies in the sample which are specific for the recombinant protein or a specific antigen bound to the solid support, a sample from a subject is incubated with the protein chip described in Example 4 in a buffered solution at neutral pH for a period of 5 minutes to overnight. Conditions permissive to the formation of antigen-antibody binding are well known in the art. The protein chip is then extensively washed in buffered solution under non-reducing conditions in order to remove proteins which are not specifically bound to the chip. Bound antibody is then removed from the solid support for further identification (i.e. SDS-PAGE) although they can also be analyzed in situ. Conditions for removal of the bound antibody are well known in the art and include but are not limited to incubation in buffer under reducing conditions.

Alternatively, recombinant antibody or an antigen binding portion thereof may be covalently bound to the solid support by the methods described herein above in order to screen a sample from a subject for a specific antigen, toxin or protein.

A great advantage of the diagnostic kit of this invention is the capability of arranging multiple substrates on the solid support array. The substrates can be variously labeled such as with flourescent tags in order to facilitate simultaneous screening and identification.

Furthermore, the nature of the covalent bond of the recombinant protein to the solid support enables a Atight@ grid which provides a signal which will not diffuse even following rigorous washings to remove non-specific interactions. This facilitates high-throughput screening, including robotic-based screening which is well-described in the art. Such screenings can identify novel drugs and therapeutic which work through or interfere with the interactions described herein. Moreover, such a support Achip@ contemplates a reusable chip which could be provided in many different forms and formats.

The following is a list of documents related to the above disclosure and particularly to the experimental procedures and discussions. The documents should be considered as incorporated by reference in their entirety.

References

1. Noren, C. J., et al., *Science* 244, 182 (1989).
2. Wallace, C. J. A., *Current Opinion in Biotechnology* 6, 403 (1995).
3. Witte, K., et al., *J. Am. Chem. Soc.* 119, 2114 (1997).
4. Jackson, D. Y., et al., *Science* 266, 243 (1994).
5. Dawson, P. E., et al., *Science* 266, 776 (1994).
6. Muir, T. W., *Structure* 3, 649 (1995).
7. Xu, M.-Q., et al., *EMBO J.* 15, 5146 (1996).
8. Chong, S., et al., *Gene* 192, 271 (1997).
9. Brown, M. T., et al., *Biochim. Biophys. Acta* 1287, 121 (1996).
10. Superti-Furga, G., et al., *Bioessays* 17, 321 (1995).
11. Boerner, R. J., et al., *Biochemistry* 35, 9519 (1996).
12. Sicheri, F., et al., *Nature* 385, 602 (1997).
13. Moarefi, et al., *Nature* 385, 650 (1997).
14. Xu, W., et al., *Nature* 385, 595 (1997).
15. Nada, S., et al., *Nature* 351, 69 (1991).
16. Partanen, J., et al., *Oncogene* 6, 2013 (1991).
17. Cole, P. A., *Structure* 4, 239 (1996).
18. Cole, P. A., unpublished data.
19. Koegel, M., et al., *Biochem. J.* 302, 737 (1994).
20. Songyang, Z., et al., *Mol. Cell. Biol.* 14, 2777 (1994).
21. Bougeret, C., et al., *J. Biol. Chem.* 271, 7465 (1996).
22. Dawson, P. E., et al.,*J. Am Chem. Soc.* 119, 4325 (1997).
23. MacAuley, et al., *Mol. Cell. Biol.* 9, 2648–2656 (1989).
24. Erlanson, D. A., et al., *Chemistry and Biology* 3, 981 (1996).
25. Kemp et al., *J. Org Chem.,* 58, 2216–2222
26. Liu et al., *J. Am. Chem. Soc.,* 116, 4149–4153
27. Schnölzer et al., *Science,* 1992, 256, 221–225
28. Gaertner et al., *Bioconjugate Chem.,* 3, 262–268
29. Muir et al., *Biochemistry,* 33, 7701–7708
30. Rose, K., *J Am. Chem. Soc.,* 116, 30–33
31. Nefzi et al., *Tetrahedron Letters,* 36, 229–230
32. Dawson et al., *Science,* 266, 776–779
33. Wallace, C. J. A., *Curr. Opin. Biotech.,* 6, 403–410
34. Schnölzer et al., *Int. J. Pept. Protein Res.,* 40, 180–193.
35. Severinov et al., *Proc. Natl. Acad. Sci. USA,* in press
36. Minchin et al., *Biochem. J.,* 289, 771–775
37. Severinova et al., *J. Mol. Biol.* 263, 637–647
38. Chong et al., *Gene,* 1997, 192, 271–281
39. Burton et al., *Nucleic Acids Res.* 9, 2889–2903
40. Gardella et al., *J. Mol. Biol.* 206, 579–590
41. Siegele et al., *J. Mol. Biol.,* 206, 591–603
42. Kumar et al., *J. Mol. Biol.,* 235, 405–413
43. Li et al., *Science,* 263, 75–77
44. Lonetto et al., *J. Bacteriol.,* 174, 3843–3849
45. Kumar et al., *J. Mol. Biol.,* 232, 406–418
46. Jaenicke, R., *Biochemistry* 30, 3147–3161.
47. Bork, P., *Trends Biochem Sci* 22, 296–298.
48. Wuthrich, K., *Nat Struct Biol* 4 Suppl, 849–53.
49. Wuthrich, K., *Nat Struct Biol* 5 Suppl, 492–5.
50. Cowburn, D., *J. Am. Chem. Soc.* 105, 7435–7442.
51. Campbell, I. D. et al., *Nat Struct Biol* 5 Suppl, 496–9.
52. Kuriyan, J. et al., *Annu Rev Biophys Biomol Struct* 26, 259–88.
53. Tjaiidra, N. et al., Science 279, 1111–4.
54. Shuker, S. B. et al., *Science* 274.1531–4.
55. Southworth, M. W., et al., *EMBO J.* 17(4), 918–926.
56. Shingledecker, K., et al., Gene 207, 187–95.
57. Mills, K. V., et al., *Proc Natl Acad Sci USA* 95, 3543–8.
58. Yamazaki, T., et al., *Am. Chem. Soc.* 120 (22), 5591–5592.
59. Severinov, K., et al., *J Biol Chem* 273, 16205–9.
60. Muir, T. W., et al., *Proc Natl Acad Sci USA* 95, 6705–10.
61. Chong, S., et al., *Gene* 192, 271–81.
62. Evans Jr., et al., *Protein Science* in press.
63. Rosenberg, N., et al., *Adv Virus Res* 35, 39–81.
64. Mayer, B. J., et al., *Mol Cell Biol* 14, 2883–94.
65. Muller, A. J., et al., *Mol Cell Biol* 12, 5087–93.
66. OverdLiin, M., et al., *Cell* 70, 697–704.
67. Gosser, Y. Q., et al., *Structure* 3, 1075–1086.
68. Dawson, P. E., et al., *Science* 66, 776–779.
69. Muir, T. W., et al., *Metllioci,@* 289, 266–298.

70. Erlanson, D. A., et al., *Chem Biol* 981–91.
71. Dawson, P. E., et al., *Am. Chem. Soc.* 119, 4325–4329.
72. Canne, L., et al., *Amer. Chem. Soc.* 118, 5891–5896.
73. Lu, W., et al., *Biochemistry,* 36, 673–679.
74. Camarero, J. A., et al., *J. Pept. Res.* 51, 303–16.
75. Hojo, H. et al., *Bull. Chem. Soc. Japan* 64, 111–117.
76. Camarero, J. P., et al., *Ang. Chem. Int. Ed.* 37, 345–348.
77. Cowburn, D., et al., *J Biol Chem* 270, 26738–26741.
78. Nam, H. J., et al., *Structure* 4, 1105–14.
79. PervLishin, K., et al., *Proc. Natl. Acad. Sci. USA* 94, 12366–71.
80. Hendrickson, W. A., *Science* 254, 51–8.
81. Prestegard, J. H., *Nat Strrct Biol* 5 Suppl, 517–22.
82. Alewood, P., et al., *Methods Enzymol* 289, 14–29.
83. Hackeng, T. M., et al., *Proc. Natl. Acad. Sci USA.* 94, 7845–7850.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of cleaving a recombinantly expressed protein bound to an intein-chitin binding domain (CBD) and ligating said cleaved recombinant protein to a peptide containing an N-terminal cysteine having an unoxidized sulfhydryl side chain said method comprising contacting said recombinatly expressed protein bound to said intein-CBD with said peptide in a reaction solution containing a conjugated thiol, thereby effecting, in a one-pot reaction, cleavage of said recombinatly expressed protein from said intein-CBD and production of a C-terminal thioester of the recombinatly expressed protein which spontaneously undergoes intramolecular rearrangement to form an amide bond linking the C-terminus of said protein to the N-terminus of said peptide, wherein said conjugated thiol is selected from the group consisting of thiophenol, 2-nitrothiophenol, 2-thiobenzoic acid, 2-thiopyridine, 4-thio-2-pyridine carboxylic acid and 4-thio-2-nitropyridine.

2. The method according to claim 1, wherein the conjugated thiol is thiophenol.

3. The method according to claim 1, wherein reaction is conducted at about pH 7.

4. The method according to claim 2, wherein reaction is conducted at about pH 7.

5. The method according to claim 1, wherein the reaction is conducted in a buffered solution.

6. The method according to claim 2, wherein the reaction is conducted in a buffered solution.

7. The method according to claim 1, wherein the recombinantly expressed protein is generated in a prokaryotic host.

8. The method according to claim 1, wherein the recombinantly expressed protein is generated in a eukaryotic host.

9. The method according to claim 1, wherein the recombinantly expressed protein is expressed by pCYB expression plasmids.

10. The method according to claim 2, wherein the recombinantly expressed protein is expressed by pCYB expression plasmids.

* * * * *